(12) United States Patent
Volek et al.

(10) Patent No.: US 11,439,555 B2
(45) Date of Patent: *Sep. 13, 2022

(54) MEDICAL TECHNOLOGY STATION AND METHOD OF USE

(71) Applicant: Capsa Solutions LLC, Canal Winchester, OH (US)

(72) Inventors: Robert Volek, Brooklyn, NY (US); Jack Finnerty, Cambridge (GB); Jin Chen, Somerset, NJ (US); Krzysztof Sosniak, Stirling, NJ (US); Marcel Ipince, North Plainfield, NJ (US); Charles Pfeiffer, Phillipsburg, NJ (US); Adam Piotrowski, Clifton, NJ (US); Harry Tan, Shanghai (CN)

(73) Assignee: Capsa Solutions LLC, Canal Winchester, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/910,988

(22) Filed: Jun. 24, 2020

(65) Prior Publication Data

US 2020/0315891 A1 Oct. 8, 2020

Related U.S. Application Data

(63) Continuation of application No. 15/975,860, filed on May 10, 2018, now Pat. No. 10,751,239, which is a
(Continued)

(51) Int. Cl.
*A61G 12/00* (2006.01)
*A61J 7/00* (2006.01)
(Continued)

(52) U.S. Cl.
CPC .......... *A61G 12/001* (2013.01); *A47B 31/00* (2013.01); *A61J 7/0084* (2013.01); *G16H 20/13* (2018.01);
(Continued)

(58) Field of Classification Search
CPC ......... A61G 12/00; A61G 12/001; A61J 7/00; G06F 19/00; G06F 19/3462; A47B 88/47; A47B 2031/006; G07F 17/0092
See application file for complete search history.

(56) References Cited

U.S. PATENT DOCUMENTS 6,175,779 B1    1/2001  Barrett
6,636,780 B1   10/2003  Haitin et al.
(Continued)

FOREIGN PATENT DOCUMENTS

CN    201070133 Y    6/2008
CN    201174189 Y   12/2008
(Continued)

OTHER PUBLICATIONS

InnerSpace, "System 100 User Guide." Publication No. SYUG-1, pp. 1-14.
(Continued)

*Primary Examiner* — Timothy R Waggoner
(74) *Attorney, Agent, or Firm* — Standley Law Group LLP; Adam J. Smith; Jeffrey S. Standley

(57) ABSTRACT

The invention includes a medical technology station and a method for using the medical technology cart. The station can be a portable cart that can be movable, such as rollable, and has a computer system. Attached to the cart is a housing that communicates with the computer system. Insertable in the housing is a cassette system that includes a series of drawers. The drawers are openable and preferably closeable on command from a user. The drawers have a readable unique drawer identifier that is readable by sensors in the cassette. The cassette also preferably includes proximity sensors, while the drawers contain a target for the proximity sensors. In use, an operator, with proper credentials, can, though the computer system, identify a drawer to be opened by the computer system. The cassette and drawers can be
(Continued)

removed from the housing and transported to another location for filling of the drawers with medications or other supplies.

17 Claims, 33 Drawing Sheets

Related U.S. Application Data

(63) continuation of application No. PCT/US2016/061911, filed on Nov. 14, 2016.

(60) Provisional application No. 62/255,336, filed on Nov. 13, 2015.

(51) Int. Cl.
| | |
|---|---|
| *G16H 20/13* | (2018.01) |
| *G16H 40/63* | (2018.01) |
| *A47B 31/00* | (2006.01) |
| *A47B 67/02* | (2006.01) |
| *G16H 40/20* | (2018.01) |

(52) U.S. Cl.
CPC .............. *G16H 40/63* (2018.01); *A47B 67/02* (2013.01); *A47B 2031/003* (2013.01); *A47B 2031/006* (2013.01); *A47B 2067/025* (2013.01); *A61G 2203/16* (2013.01); *A61G 2203/20* (2013.01); *A61G 2205/60* (2013.01); *G16H 40/20* (2018.01)

(56) References Cited

U.S. PATENT DOCUMENTS

| | | | |
|---|---|---|---|
| D486,915 S | 2/2004 | Warschewske et al. | |
| 7,155,306 B2 | 12/2006 | Haitin et al. | |
| 7,440,818 B2 | 10/2008 | Handfield et al. | |
| 7,594,668 B2 | 9/2009 | Arceta et al. | |
| 7,630,790 B2 | 12/2009 | Handfield et al. | |
| 7,630,791 B2 | 12/2009 | Nguyen et al. | |
| 7,693,603 B2 | 4/2010 | Higham | |
| 7,719,420 B2 | 5/2010 | Christie et al. | |
| 7,721,914 B2 | 5/2010 | Handfield et al. | |
| 7,735,681 B2 | 6/2010 | Handfeld et al. | |
| 7,735,683 B2 | 6/2010 | Handfield et al. | |
| 7,751,933 B2 | 7/2010 | Handfield et al. | |
| 7,844,362 B2 | 11/2010 | Handfield et al. | |
| 7,860,583 B2 | 12/2010 | Condurso et al. | |
| 7,860,603 B2 | 12/2010 | Handfield et al. | |
| 7,862,534 B2 | 1/2011 | Quirico et al. | |
| D632,797 S | 2/2011 | Ross et al. | |
| 7,886,931 B2 | 2/2011 | Handfield et al. | |
| 7,908,030 B2 | 3/2011 | Handfield et al. | |
| 7,909,207 B2 | 3/2011 | Handfield et al. | |
| 7,919,246 B2 | 3/2011 | Handfield et al. | |
| 7,949,426 B2 | 5/2011 | Handfield et al. | |
| 7,996,105 B2 | 9/2011 | Handfield et al. | |
| 8,027,748 B2 | 9/2011 | Handfield et al. | |
| 8,027,749 B2 | 9/2011 | Vahlberg et al. | |
| 8,073,563 B2 | 12/2011 | Vahlberg et al. | |
| D652,521 S | 1/2012 | Ross et al. | |
| 8,090,473 B2 | 1/2012 | Higham | |
| 8,103,379 B2 | 1/2012 | Biba et al. | |
| 8,112,175 B2 | 2/2012 | Handfield et al. | |
| 8,126,590 B2 | 2/2012 | Vahlberg et al. | |
| 8,131,397 B2 | 3/2012 | Vahlberg et al. | |
| 8,140,186 B2 | 3/2012 | Vahlberg et al. | |
| 8,155,786 B2 | 4/2012 | Vahlberg et al. | |
| 8,180,485 B2 * | 5/2012 | Reckelhoff | G16H 20/13 700/242 |
| 8,196,939 B2 | 6/2012 | Bustle et al. | |
| 8,210,548 B1 | 7/2012 | Agyemang | |
| 8,215,650 B2 | 7/2012 | Arceta et al. | |
| 8,239,062 B2 | 8/2012 | Vahlberg et al. | |
| 8,280,550 B2 | 10/2012 | Levy et al. | |
| 8,292,807 B2 | 10/2012 | Perkins et al. | |
| 8,335,588 B2 | 12/2012 | Rahilly et al. | |
| 8,340,792 B2 | 12/2012 | Condurso et al. | |
| 8,353,456 B2 | 1/2013 | Jackson et al. | |
| 8,376,478 B2 | 2/2013 | Weber et al. | |
| 8,380,346 B2 | 2/2013 | Chudy et al. | |
| 8,384,545 B2 | 2/2013 | Hussain et al. | |
| 8,517,215 B2 | 8/2013 | Shafir | |
| 8,554,365 B2 | 10/2013 | Thomas et al. | |
| 8,558,659 B2 | 10/2013 | Ross | |
| 8,560,117 B2 | 10/2013 | Handfield et al. | |
| 8,588,964 B2 | 11/2013 | Garda et al. | |
| 8,588,966 B2 | 11/2013 | Michael | |
| 8,593,278 B2 | 11/2013 | Churbock et al. | |
| 8,630,722 B2 | 1/2014 | Condurso et al. | |
| 8,686,859 B2 | 4/2014 | Hussain et al. | |
| 8,700,210 B2 | 4/2014 | Bufalini et al. | |
| 8,701,921 B2 | 4/2014 | Acedo Morono | |
| 8,706,294 B2 | 4/2014 | Rahilly et al. | |
| 8,708,352 B2 | 4/2014 | Quirico et al. | |
| 8,712,587 B2 | 4/2014 | Handfield et al. | |
| 8,731,958 B2 | 5/2014 | Barrett et al. | |
| 8,744,621 B2 | 6/2014 | Michael | |
| 8,761,906 B2 | 6/2014 | Condurso et al. | |
| 8,770,479 B1 | 7/2014 | Shoenfeld | |
| 8,773,270 B2 | 7/2014 | Paydar et al. | |
| 8,818,522 B2 | 8/2014 | Heffron | |
| 8,842,183 B2 | 9/2014 | Glickman et al. | |
| 9,155,682 B2 | 10/2015 | Boyd | |
| 9,367,984 B2 | 6/2016 | Daugbjerg et al. | |
| 9,474,670 B2 | 10/2016 | Pamplona Rovira | |
| 10,751,239 B2 * | 8/2020 | Volek | G16H 20/13 |
| 2006/0079994 A1 | 4/2006 | Chu et al. | |
| 2006/0125356 A1 * | 6/2006 | Meek, Jr. | G16H 40/67 312/215 |
| 2011/0234419 A1 | 9/2011 | Churbock et al. | |
| 2012/0232692 A1 | 9/2012 | Liu et al. | |
| 2013/0018505 A1 * | 1/2013 | Barrett | A61G 12/001 700/231 |
| 2013/0331983 A1 | 12/2013 | Barrett et al. | |
| 2014/0197954 A1 | 7/2014 | Caputo et al. | |
| 2015/0042217 A1 | 2/2015 | Olson | |
| 2015/0227127 A1 * | 8/2015 | Miller | G16H 20/13 700/244 |

FOREIGN PATENT DOCUMENTS

| | | |
|---|---|---|
| CN | 202236074 U | 5/2012 |
| CN | 202478056 U | 10/2012 |
| CN | 202515778 U | 11/2012 |
| CN | 202568713 U | 12/2012 |
| CN | 202618804 U | 12/2012 |
| CN | 104003048 A | 8/2014 |
| EP | 1786350 A2 | 5/2007 |
| EP | 2174251 A2 | 4/2010 |
| TW | 200911198 A | 3/2009 |
| TW | 201237800 A | 9/2012 |
| WO | 2009009698 A2 | 1/2009 |

OTHER PUBLICATIONS

International Search Report and Written Opinion by the International Searching Authority for PCT Application PCT/US2016/61911 dated May 15, 2017.

CareDirect—Medication Dispensing Cabinets, retrieved from https://www.caredirectllc.com/ on Jun. 19, 2019, pp. 1-6.

* cited by examiner

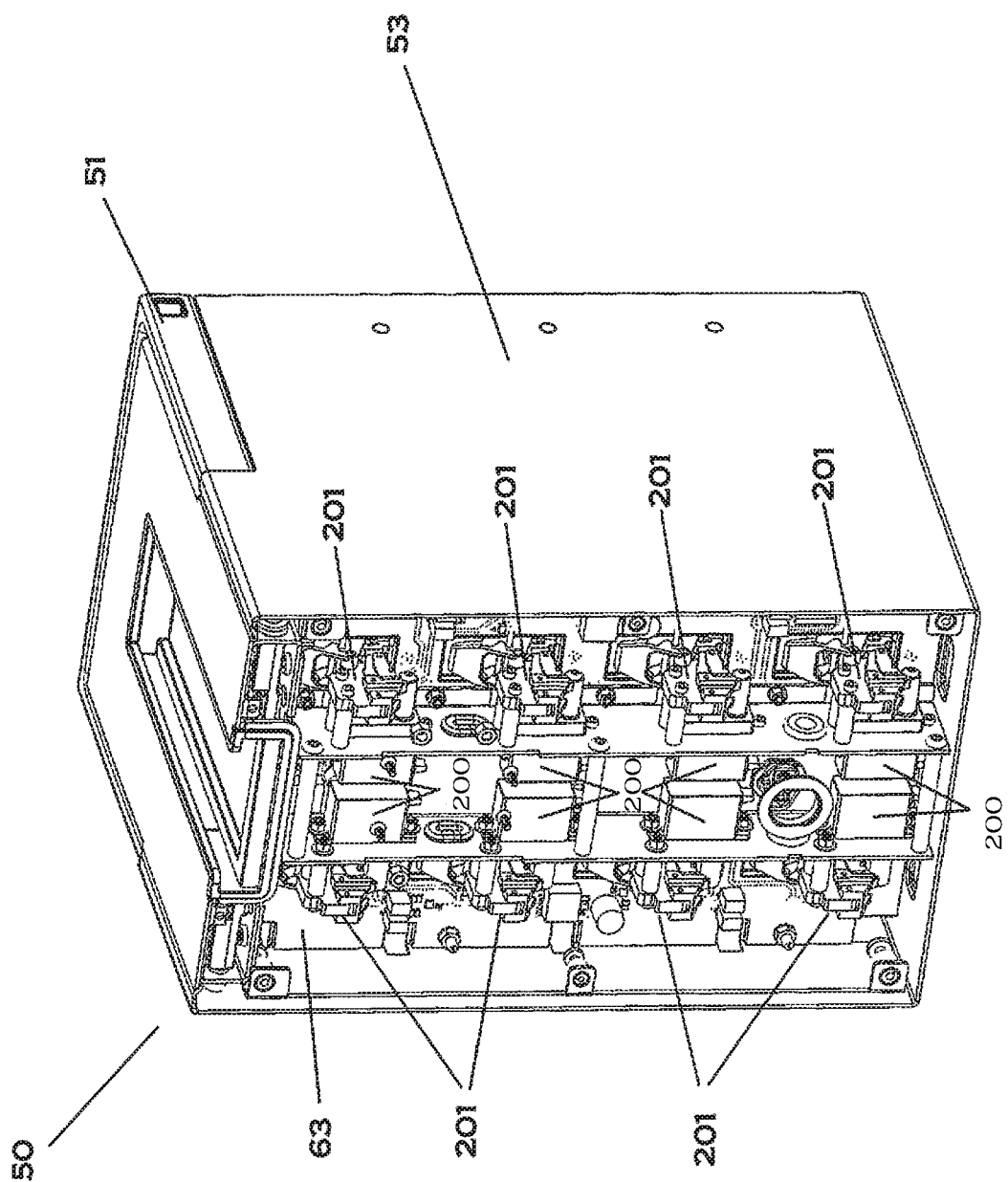

Figure 15A Cassette ejection – MedLink Lite

| | User action/user display | System Computer Action |
|---|---|---|
| 1 | In Cassette View, touch the eject button in the center of the cassette graphic. | Receive request to eject cassette |
| 2 | The cassettes will highlight in blue. Touch the cassette you wish to eject. | Update screen<br><br>Send command to eject selected cassette on the system bus |
| 3 | The cassette handle will pop out of the housing, allowing you to remove it. Continue to eject additional cassettes if required, or touch the Cancel button to return to Cassette View. | Poll system<br><br>Cassette fails to respond |
| 4 | Remove the cassette from the housing by pulling the handle outwards. | Update screen to show cassette as empty |
| 5 | On returning to Cassette View, you will see the ejected cassette is shown as empty on the graphic with no label. Any labelled drawers that were in the removed cassette will also be removed from the drawer list, as they are no longer available. | (note on re-insertion, system will recognize drawers that were stored in local memory, but not new drawers. New drawers will be displayed as an unassigned drawer, and the local table will be updated accordingly) |

Figure 15B Cassette ejection – MedLink Pro

|   | User action/user display | System Computer Action |
|---|---|---|
| 1 | Click the icon on top of the cassette to eject that cassette. Note that all drawers on the chosen cassette much be locked first. If user does not have credentials, the eject icon will be disabled. | Verify credentials of user to allow removal of cassette. If no credentials, disable eject button.<br><br>Receive Request to eject cassette<br><br>Verify status of all drawers as closed |
| 2 | The cassette handle will pop out of the housing, allowing you to pull the cassette out and remove it. | Send eject handle command on system bus |
| 3 | Remove the cassette from the housing by pulling the handle outwards. | Poll system, discover cassette removed |
| 4 | The screen will update to show the cassette has been removed. | Update screen to show cassette removed.<br><br>(On reinsertion of a cassette, system will discover new cassette then poll for cassette drawer information (RFID, size), request drawer identifier/patient identifier from server, and repopulate server table with new configuration, and refresh display with new configuration data) |

Figure 16A Drawer opening – MedLink Lite

| | User action/user display | System Computer Action |
|---|---|---|
| 1 | In Drawer View, to open a drawer first select the drawer, either by touching the label in the drawer list or touching on the drawer in the cassette graphic. In Cassette View, you may also touch a label in the drawer list. | (a) Receive open command<br>(b) Find drawer location in local table |
| 2 | The selected drawer and its label will highlight in gray, helping you to locate the drawer on the physical drawer system.<br>NOTE: With the drawer selected, touch the Open button. From the drawer selected screen, you may also re-label drawers by touching the Edit Label button. | |
| 3 | The drawer will unlock ready to be removed and the cassette graphic will update to show the drawer in blue. The drawer auto close timer will display on screen, along with the drawer label, allowing you to confirm which drawer you have opened. If the timer reaches zero the drawer will automatically relock. You may also touch the Lock button to relock the drawer without removing it.<br>With a patient drawer unlocked, touch a storage drawer to first select it, then touch the Open button to open it. The storage drawer will unlock, and both drawers will be highlighted blue on the cassette graphic. | (a) Send open command<br>(b) Poll system<br>(c) Update drawer status on output screen to show drawer unlocked, update drawer status in local table<br>(d) Initiate timer for autoclose<br>(e) Prompt user with notification of time to autoclose<br>(f) Poll status, if drawer status does not change in time interval, send close drawer command and update drawer status on screen |
| 4 | On opening or removing the drawer the display will revert to Drawer View with the drawer list and cassette graphic showing a blank label to indicate there is no drawer present. | (a) Poll status, if drawer status changes to open<br>(b) Update drawer status on screen and local table |
| 5 | When the Open All function is enabled, the Open All button is displayed in Drawer View. This allows the user to unlock all the drawers in that cassette at once. This should only be used when emptying the cassette of medication. Opening more than more drawer containing patient medication while administering risks the wrong medication being used.<br>In Drawer View, touch the Open All button to begin the process. | (a) Receive open all command,<br>(b) Identify cassette |
| 6 | You will be warned that opening all the drawers should only be done when emptying | (c) Send warning message to screen |

|   | | |
|---|---|---|
|   | the cart. Touch OK to acknowledge the warning. | |
| 7 | There are several options when opening all the drawers. You may open all the drawers and retain all the drawer labels, open all the drawers and erase the patient labels but keeping the storage drawer labels, or erase all the labels. Touch an option to continue. | (a) Receive option from user, execute selected option (modify information in local table on drawers) |
| 8 | All the drawers on the chosen cassette will unlock and highlight in blue on the cassette graphic. Drawers maybe removed and emptied. If drawers are not opened or removed, when the re-lock timer reaches zero they will automatically re-lock. | (a) Receive open all command, (b) send open all command to housing with cassette address |
| 9 | If you selected an option such as "Open all & Erase all labels" the appropriate labels will be missing when the drawers are replaced. | Execute option is selected |

Figure 16A continued

Figure 16B Drawer opening – MedLink Pro

| | User action/user display | System Computer Action |
|---|---|---|
| 1 | When you are with the patient and ready to administer medication, scan the patient's wristband bar code. Ensure the MedLink window is in the currently active window, otherwise the bar code scan input will not reach the MedLink software. | (a) Receive scanned bar code, (b)retrieve RFID information associated with patient from the server, based on patient barcode (c)locate drawer(s) in cart (housing, cassette and compartment) (d)verify user credentials for authorization to open drawer(s) |
| 2 | If drawer(s) assigned to that patient are detected in the cart, the drawer(s) will automatically unlock. The screen will display the auto close timer. If no further action is taken as this point, the drawer will relock, securing the medication. | (a) If user authorized and drawer(s) located, send open drawer command on bus (b) Poll system status (c) Update drawer status on output screen to show drawer unlocked, update drawer status in local table (e)Initiate timer for auto close (f)Prompting user with notification of time to auto close (g)Poll status, if the drawer(s) status does not change in timed interval, send close drawer command on bus, and update drawer status on screen as closed (h)If drawer(s) are removed, auto close timer closes. |
| 3 | If a barcode is damaged or unavailable to scan and you need to access a drawer, begin by selecting a drawer and clicking the Open button. On the following screen where you are prompted to scan a barcode to continue, click the Cannot scan barcode button.<br>• You will be prompted to enter the login credentials of a colleague or to enter the patient's PAN or MRN number to record that you are opening a drawer without the security of scanning a bar code.<br>• Once the credentials have been accepted, on the next screen enter the reason you cannot scan the appropriate bar code.<br>• On clicking Continue, the drawer will unlock and you can continue to fill or administer medication as needed. | (a) System received request to open drawer without a location barcode scan. Displays screen informing user of needed scan with option for manual override.<br><br>User selects "Cannot scan barcode" button.<br>(b) System shows preconfigured screen (either witness override or PAN / MRN override.<br>(c) System obscures PAN/MRN if shown on center screen.<br>(d)System validates witness credentials or PAN/MRN to server.<br>(e)If credentials pass system will display Reason screen asking for the reason (if configured)<br>(f)System will then send command on bus to open the selected drawer.<br>(g)System will display auto close timer |
| 3 | Pull the drawer out and remove it completely if you wish. The screen will update, indicating the drawer has been removed. At this point | (a)If drawer status changes during time interval, (eg. to open or closed) – refresh screen to reflect new drawer status and store |

|   | you can go ahead with your normal medication administration process. | new drawer status in server table |
|---|---|---|
| 4 | With a patient drawer(s) open, you may also open storage drawers to access supplies and consumables needed to administer the medication. Simply click on a storage drawer to unlock it. | (a)Receive user input to open storage drawer<br>(b) Verify user is allowed to access storage drawer (server database)<br>(c)Locate storage drawer in cart (housing, cassette compartment)<br>(e) If user authorized and drawer located, send open drawer command on bus<br>(f) Poll system status<br>(g)Update drawer status on output screen to show drawer unlocked<br>(h)If drawer status changes, refresh screen to reflect new drawer status |
| 5 | As long as a patient drawer is open, the on-screen prompt will remain, advising the user to return the patient drawer to continue. This ensures that only one patient drawer may be opened at a time, thereby preventing the possibility of medication getting mixed between patient drawers. A single patient may have more than one drawer assigned. All assigned drawers to a single patient will open on wrist band scan. | (a) Poll status for drawer<br>(b)Update screen with return drawer message |
| 6 | When the patient drawer(s) are return to the cassette, the process ends and the screen returns to the home screen. | (a)Poll status<br>(b)Detect drawer, send request to server for drawer identifiers, update screen with received identifiers, update status on screen and in server table<br>(c)If drawer status non-retracted, Initiate timer for auto close<br>(d)Prompt user with notification of time to auto close<br>(e)Poll status, if drawer status does not change in time interval, send close drawer(s)<br>(f) command on bus, and update drawer status on screen (will close all unlocked drawers) |
| 7 | Storage drawers may be unlocked at any time without scanning a bar code by clicking on the drawer, and then clicking the Open button. Note: Storage drawers may be configured to unlock automatically with patient drawer(s) or on login. | (a) System sends command on bus to selected storage drawer. |

Figure 16B continued

Figure 17A Drawer assignment/labeling – MedLink Lite

| | User action/user display | System Computer Action |
|---|---|---|
| 1 | In order to label a drawer to store a patient's medication, go to Drawer View for the cassette you wish to use. In the list on the right hand portion of the display, touch the Add Label icon that corresponds to the drawer you wish to label. | (a) Receive request to add label |
| 2 | You will be presented with a list of options for labelling the drawer. Touch "Enter drawer label". <br><br> To label a drawer as a storage drawer instead of a patient drawer, touch "Label drawer as STORAGE". | (a) Refresh screen with add label options <br><br> (b) Receive users option selection |
| 3 | This will take you to the label entry screen. Use the on screen keyboard to enter an appropriate label. You might want to use the patient's last name, both first and last names, or room number for example, or a descriptive label if you are labelling a storage drawer. There are no restrictions on the text you may enter. When you are done entering the label touch the Save button. | (a) Refresh screen with labeling options <br><br> (b) Accept user input, update local table with entered label information (local table contains RFID information and stored label information) |
| 4 | The display will return to Drawer View and if successful, you will see that the list shows the new label you entered, and the corresponding drawer on the cassette graphic is highlighted in bold. <br><br> If you labelled a drawer as a storage drawer, you will see the drawer in the drawer list and on the cassette graphic is represented by being underlined and having uppercase text. This is to visually differentiate storage drawers and prevent you mistaking them for a drawer containing patient medication. | (a) Refresh screen, displaying new label information |
| 5 | On returning to Cassette View you will see the new drawer label is shown in the list, and the cassette that contains the drawer is highlighted bold. | |

Figure 17B Drawer assignment – MedLink Pro

| | User action/user display | System Computer Action |
|---|---|---|
| 1 | Ensure you are near to your Automated Dispensing Cabinet or in your medication store room and have access to the MedLink location bar code. On logging in to the software you will be presented with the home screen. | (a) System validates user credentials on server<br><br>(b) If user validated, system shows home screen |
| 2 | Scan the location bar code as prompted to tell the system you are in a designated location for assigning and filling drawers. | (a) Receive bar code, verify location from server as appropriate for desired actions<br><br>(b) Verify credentials of user for ability to change drawer assignments |
| 3 | When the location bar code is successfully scanning the center icon will change to blue. Click on screen on a currently unassigned drawer that you wish to assign to a patient. | (a) System displays Action screen for choosing assignment type<br><br>(b) Receive request to assign a drawer<br><br>(c) Locate drawer identifier in server table and recover RFID |
| 4 | The selected drawer will highlight in blue and the center prompt area will change, giving you the choice of assigned this drawer to a patient, storage or an unassigned drawer.<br><br>• Click the Patient button, or<br>• Click on the Storage button<br>• Click on the Unassign button | (a) If assignment function is invoked, update screen to show assignment options |
| 5 | The screen will now display a list of patients within the hospital than can selected and assigned to the drawer.<br><br>• By default, the list shows only patients from the current user's department.<br>• The list may be expand using the drop down menu to include patients from all departments, or patients from a different department. | Auto selection<br><br>(a) if patient assignment is requested by user, retrieve patient information from the server database and display on screen<br><br>Note: hospital information system (HIS) is inserted into the server database as it happens. |

|   |   |   |
|---|---|---|
|   | • The list may be searched using the text box.<br><br>• If the patient is not found in the list, a drawer may be manually labelled using the button in the top right. Note that when using this option, drawers do not display any information other than the label you enter, and it will not be possible to open the drawer using patient wristband scanning, since there will not be a wristband bar code associated with the drawer.<br><br>If you selected Storage, the screen will to allow you to enter a label for the storage drawer. Enter a label and click the Save button. | Manual selection<br><br>(a) Display selection parameters on screen for either Patient or Storage drawer |
| 6 | Select your chosen patient and then click the Assign button.<br><br>If you entered a Storage label or Patient Name, click Save. | Auto selection<br><br>(a) Receive patient selection from server database<br><br>(b) See table 16B for drawer open sequence.<br><br>Drawer to be assigned must be removed before assignment can continue<br><br>Manual Selection<br><br>(a) Accept identifiers for drawer, send patient identifiers/drawer identifier to server to update records.<br><br>(b) See table 16B for drawer open sequence. |
| 7 | Fill the drawer with that patient's medication and return the drawer to the cassette as prompted, ensuring it locks into place. | (a) See figure 16B for close drawer function |
| 8 | You will be returned to the home screen, and on screen the selected drawer will now show the details of the patient you chose, or the storage label you entered. The assigning and filling process is now complete. |   |

Figure 17B continued

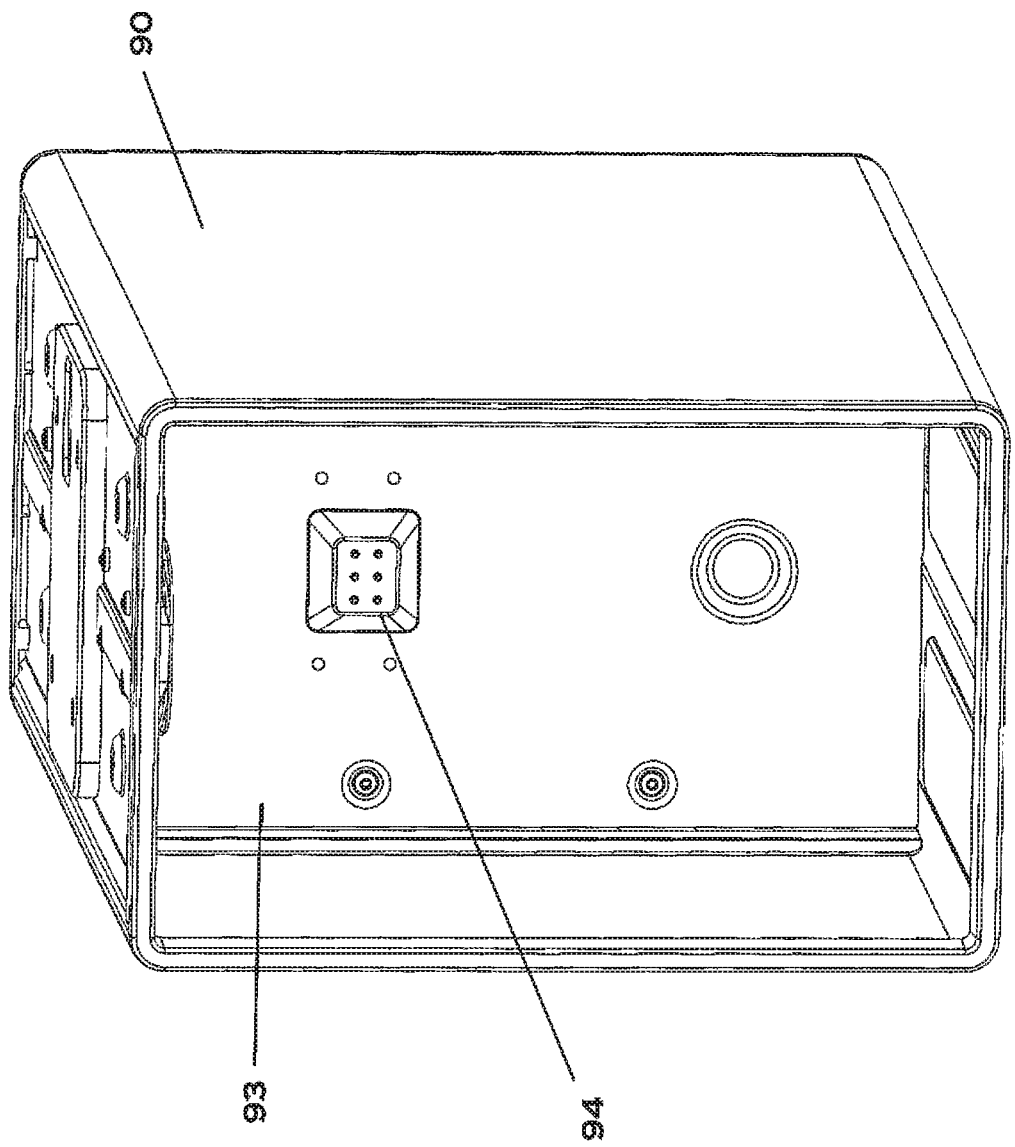

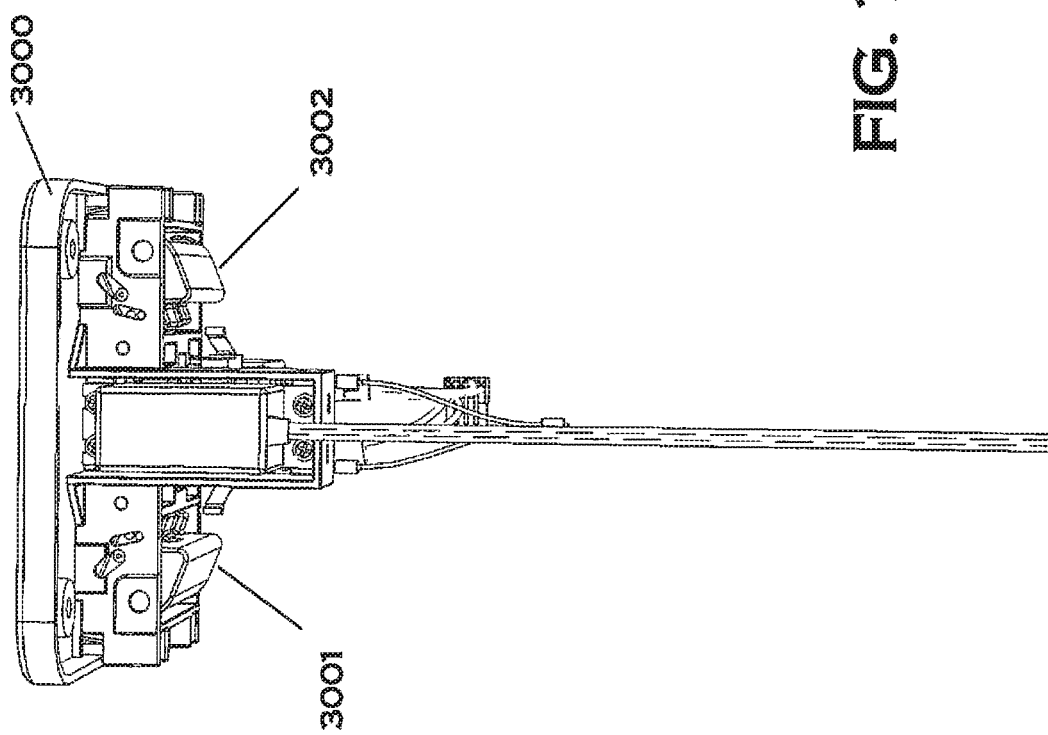

MEDICAL TECHNOLOGY STATION AND METHOD OF USE

I. CROSS REFERENCE TO RELATED APPLICATIONS

This application is a continuation of U.S. Non-Provisional application Ser. No. 15/975,860, filed on May 10, 2018, which is a continuation of PCT/US16/61911 filed on Nov. 14, 2016, which application claims the priority benefit of U.S. Provisional Application Ser. No. 62/255,336 filed on Nov. 13, 2015, all of which are incorporated by reference herein in their entirety.

II. BACKGROUND

Prescriptions are dispensed in hospitals, nursing homes and other institutions generally by hand. Nurses and medical staff will collect the needed medication at an internal pharmacy, such as at an automated dispensing cabinet (an "ADC," a vending machine-style cabinet located in a ward that dispenses medication to nurses once it is prescribed for a patient). The nurse will collect the medications for each patient for distribution. The medications can be temporarily stored in a cup for dispensing, or other temporary storage device. The nurse will then dispense the medication to patients when doing his/her rounds. These methods of delivering medication have inherent distribution errors, and these errors can result in patients consuming the improper medication or incorrect dosage, with possible adverse drug reactions, including death. A better distribution system is needed to reduce distribution errors.

III. SUMMARY

The invention disclosed herein is directed to a medical technology station for prescription dispensing and a method of using the station. The station uses a mobile wheeled cart that includes a number of assorted and reconfigurable drawers, where each drawer will generally be assigned to a single patient for a given medication distribution workflow. The drawers on the cart are electronically recognizable, by employing a unique identifier, such as inclusion of an RFID tag in each drawer, or another electronic identification device. The station's drawers are generally kept in a locked inaccessible state, unless electronically opened in response to certain preset activation signals. The station includes a display device, such as a monitor or tablet interface. The station also includes an input device, such as a keyboard, mouse, or touch screen. Optionally, the system can include a reader or scanner for barcodes or hash tags. The system also includes a processor and computer memory to interface the station equipment. The processor and equipment may be located at the station, such as a tablet or laptop. The computer memory may be located on the cart, remote from the cart, or both. The processor is in communication with the memory. The dispensing station uses a novel cassette system to accommodate the drawers within the mobile station.

In use, each patient along a distribution workflow will be assigned one or more particular drawers on the cart, such as by entry of the patient identifier and/or an associated drawer identifier into the system's memory. In use, the medical staff will preferably take an unloaded cart to a dispensing station (such as the ADC internal pharmacy). The staff loads the drawers with medication to be delivered. For instance, at the pharmacy, the medical staff will log into the cart station. The staff will enter a patient ID to access that patient's drawer, open that patient's drawer, and load the predetermined patient medication. This process is repeated until all patients' drawers are each loaded with their medications. Alternatively, all drawers can be opened at once, or all drawers in a particular cassette will be opened, and the staff will load each drawer with the medication for the patient assigned to each drawer. To dispense the medications, the staff will then roll the loaded station to particular patient's location, access the drawer using one of the input devices (to identify the patient or drawer), and dispense that patient's medication. The system includes safety features, for instance, the drawers lack pulls or handles and can only be opened electronically by a credentialed (authorized) user and, in some embodiments), one or more patient identifiers are required to open specific drawers; an authorized user's inability to access different patient's drawers at the same time; and the automatic retraction and closure of a drawer that has not been fully opened within a predetermined period of time.

The above summary is not intended to describe each illustrated embodiment or every possible implementation. These and other features, aspects, and advantages of the present invention will become better understood with regard to the following description, appended claims, and accompanying drawings.

IV. BRIEF DESCRIPTION OF THE DRAWINGS

The accompanying Figures, where like reference numerals refer to identical or functionally similar elements throughout the separate views, serve to illustrate further various embodiments and to explain various principles and advantages in accordance with the present invention:

FIG. 5 is a rear perspective view of a cassette with the rear panel removed.

FIG. 15A is a table depicting one sequence of steps to eject a cassette.

FIG. 15B is a table depicting another sequence of steps to eject a cassette.

FIG. 16A is a table depicting one sequence of steps to open a drawer.

FIG. 16B is a table depicting another sequence of steps to open a drawer.

FIG. 17A is a table one sequence of steps to assign identifiers to a drawer.

FIG. 17B is a table another sequence of steps to assign identifiers to a drawer.

FIG. 18A is a front perspective view of one embodiment of the hollow housing.

FIG. 18C is a side elevation of the one embodiment of a cassette handle actuator.

V. DETAILED DESCRIPTION

Figure 1:
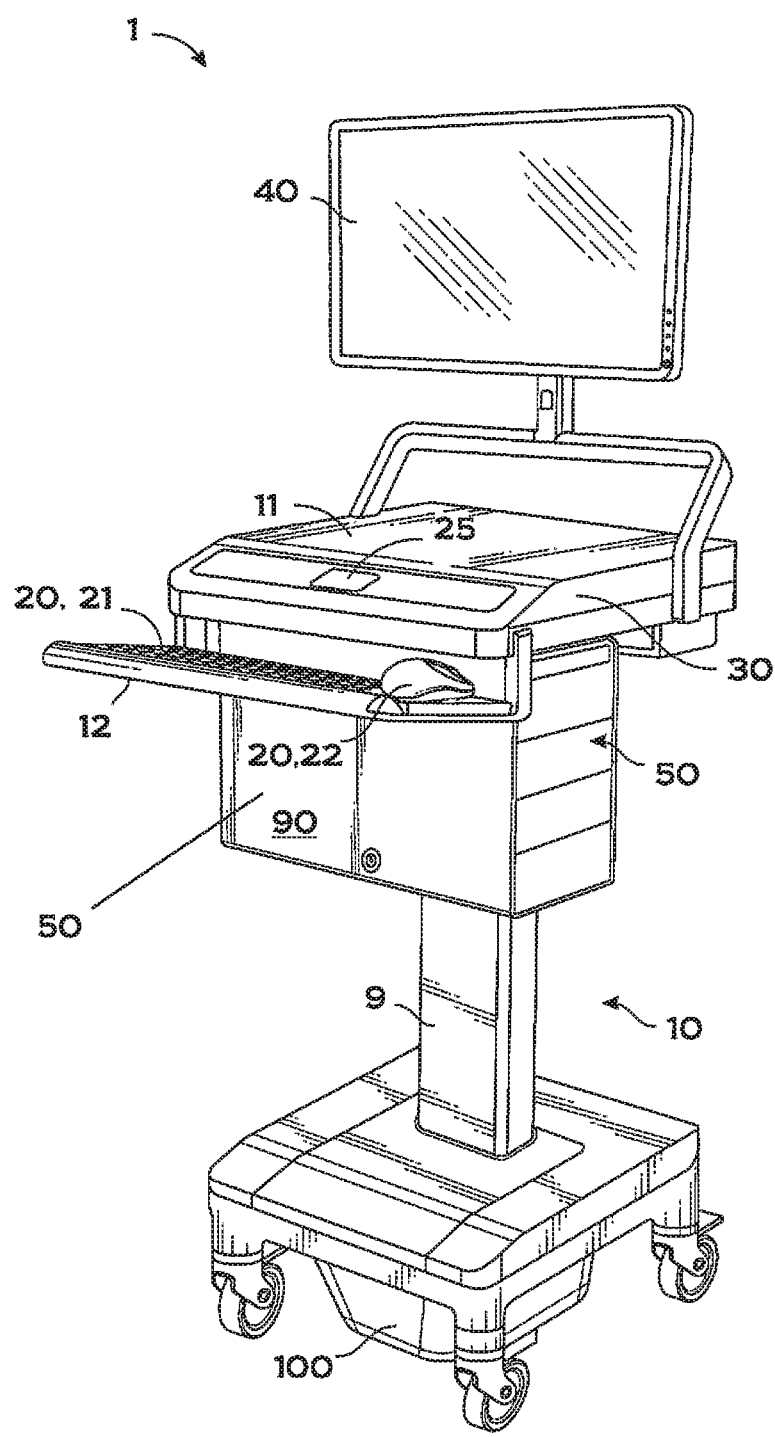
FIG. 1 is a perspective view of one embodiment of the dispensing station.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Alternate embodiments may be devised without departing from the spirit or the scope of the invention. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing Figures, in which like reference numerals are carried forward.

As used herein, the terms "a" or "an" are defined as one or more than one. The term "plurality," as used herein, is defined as two or more than two. The term "another," as used herein, is defined as at least a second or more. The terms "comprises," "comprising," or any other variation thereof are intended to cover a non-exclusive inclusion, such that a process, method, article, or apparatus that comprises a list of elements does not include only those elements, but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including," "having," or "featuring," as used herein, are defined as comprising (i.e., open language). The term "coupled," as used herein, is defined as connected, although not necessarily directly, and not necessarily mechanically. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant Figure. Relational terms such as first and second, top and bottom, right and left, and the like may be used solely to distinguish one entity or action from another entity or action without necessarily requiring or implying any actual such relationship or order between such entities or actions. Defined terms include:

ADC—Automated Dispensing Cabinet. A vending machine-style cabinet located in a ward that dispenses medication to nurses once it is prescribed for a patient. A common brand of ADC is Pyxis—ADCs are often referred to as Pyxis machines.

BCMA—Bar Code Medication Administration. A term used to describe a system where medication is bar coded and scanned prior to being administered to a patient to ensure it is the right drug/dosage.

Closed loop system—used to describe any workflow where there is end to end traceability and accountability throughout the medication distribution process.

HIS—Healthcare Information System. An umbrella term used to refer to software that stores hospital and patient information, usually accessed via the hospital's communications network.

HL7 integration—one software communications protocol for sharing patient information between different software applications. The disclosed station can use HL7 to retrieve patient information from a hospital's HIS.

Unit dose—A single pill, syringe or vial of medication, individually packaged in its lowest common dosage. This is increasingly the type of medication used in hospitals and stored in medication drawers.

Workflow—the series of steps necessary to complete a specific process, such as getting medication from an ADC to a patient.

Drawer—A removable storage cubicle that is contained in a cassette. A drawer will occupy one or more compartments. In one embodiment each drawer may be assigned to a single patient, or designated as a storage drawer. Each drawer can be opened individually through commands entered in the system by an authorized user. In a preferred embodiment, each drawer contains at least one electronically readable identifier, such as contained in an RFID tag or bar code, which is used to electronically identify the drawers. In one embodiment, there are 3 sizes of drawers.

Cassette—A cassette is a storage frame into which drawers are loaded. Cassettes are removable from the station, and in one embodiment, the cassette is removable from the cart through commands to eject the cassette handle. Cassettes are in electronic communication with the station's processor. The interior of each cassette is subdivided into compartments. Drawers inserted into the cassette occupy one or more compartments. In one embodiment, each cassette has shelves which can be removed to allow for different drawer configurations.

Compartment—a portion of the interior of a cassette that is adapted to accommodate the smallest drawer size. The cassette embodiments depicted have eight compartments, but could have more or less.

Figure 1A:
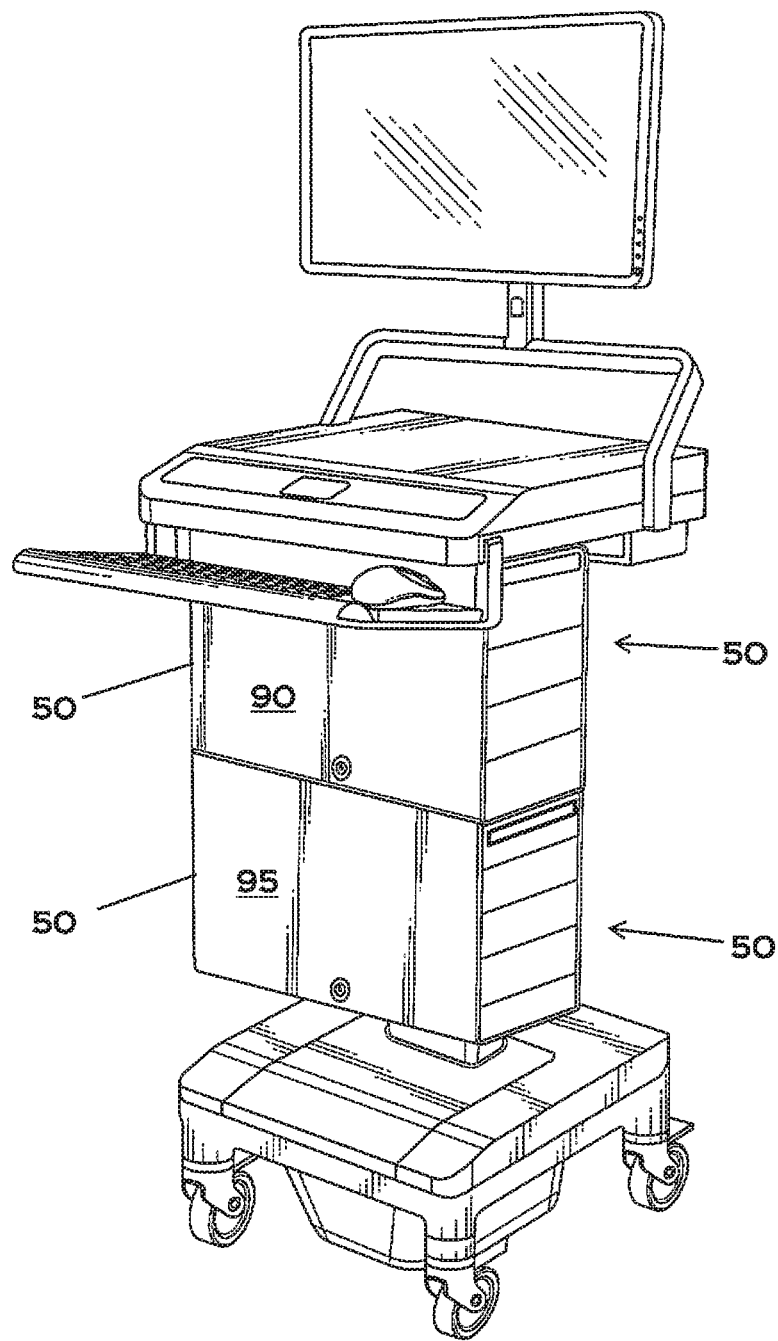
FIG. 1A is a perspective view of another embodiment of the dispensing station.

Housing—The housing is the large hollow module fixedly attached to the cart. In one embodiment, cassettes are loaded or mounted in the housing from the left and right hand sides of the station. A lower housing can be attached to an upper housing for a high capacity station, such as shown in FIG. 1A.

Location bar code—a bar code or hash code that can be placed in the hospital in specific areas. Some areas may be designated as "safe areas" to fill and restock medication drawers. For instance, a location bar code may be placed next to an ADC. Within the station's software, users can be prompted to scan location bar codes to unlock the drawers to initiate the filling or restocking process.

Figure 21:
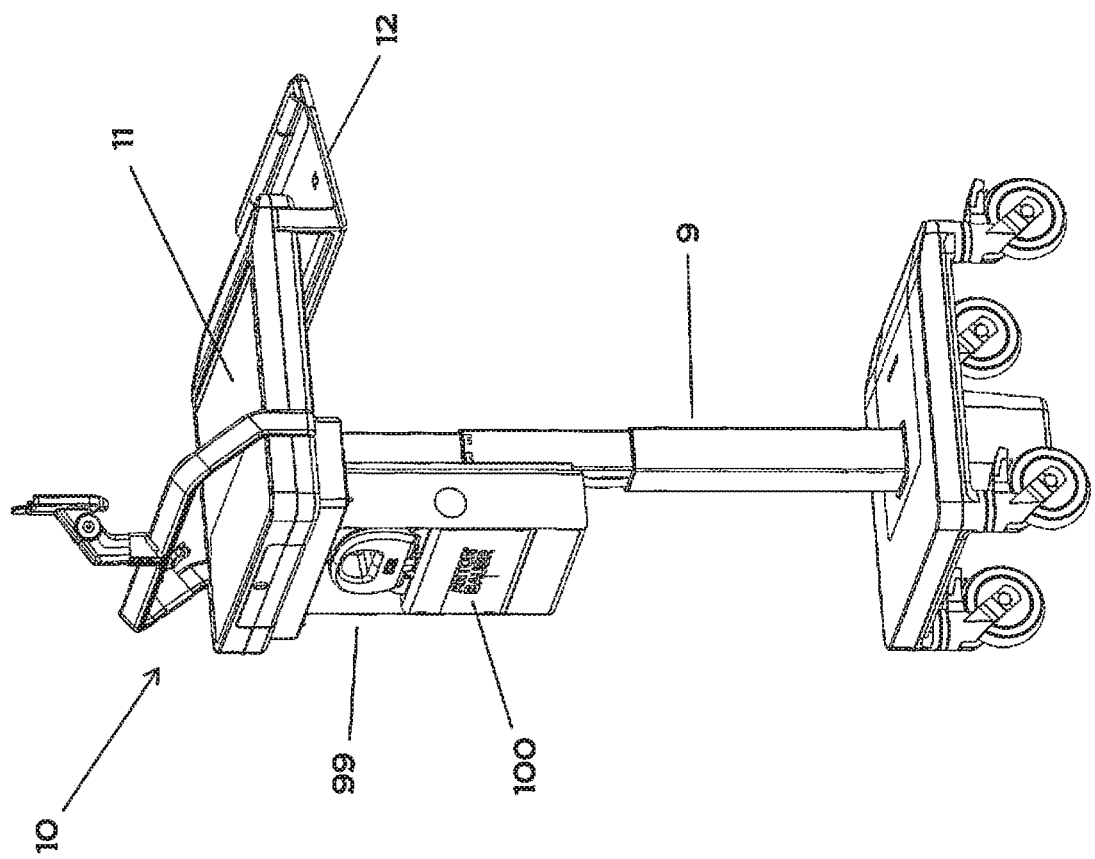
FIG. 21 is a prospective view a cart with a battery bridging station attached.

Described now are exemplary embodiments of the present invention. One embodiment of the station 1 is shown in FIG. 1. The station 1 preferably includes a movable cart, such as a rollable cart 10, where movement is provided by wheels or casters at the base of the cart. One preferred cart is a Humanscale T7 cart, which is based on the adjustable features described in U.S. Pat. No. 9,038,549, hereby incorporated by reference in its entirety. The T7 cart includes a portable power source 100, such as a rechargeable battery, generally stored in the bottom of the cart. In other embodiments, a power station, including a battery, and a battery bridge station 99 containing an internal battery, such as an Elora battery interface available from Anton Bauer of Vitec Group Plc, of Richmond UK, can be mounted to the back of the station or cart. See FIG. 21. The battery bridge allows a user to swap out a discharged battery without losing power to the cart (via the internal battery of the bridge) during the swap. The T7 cart is height adjustable (generally electronically adjustable via system software) with a center telescoping support stand 9. Preferably located on the cart 10 is a computer system comprising one or more input devices 20, a local onboard processor 30 and computer memory, and a visual display device 40. The input device 20, a local onboard processor 30, the computer memory and visual display device 40 can be a single unit, such as a tablet or laptop, or separate units. In other embodiments, a movable cart is not used, and the station (including the computer system, housing and cassette, as later described, is a stand-alone device generally located at a fixed location (such as in a pharmacy).

As shown, the cart 10 includes a work surface 11 and a keyboard mount or shelf 12 extending outwardly from the main body of the cart 10. In the embodiment of FIG. 1, a monitor 41 is mounted on a pivotable arm 15 above the work surface 11. Located on the cart is a computer, including a processor, local computer memory, input/output and display device. Shown on the keyboard mount 12 are input devices, such as a keyboard 21 and mouse 22. In the embodiment shown, a laptop or tablet can be located on the work surface or below the work surface. Also shown in FIG. 1 is a second processing device, display, and input device, represented by a tablet 25 with a touch screen interface.

In one embodiment, attached to the underside of the work surface 11 is an upper cassette housing 90, into which removable cassettes 50 can be inserted. As shown in FIG. 4D, the cassette housing 90 is a hollow rectangular shell having two opposing open sides (a right and a left open side, the right side is shown in FIG. 4D). As shown in FIG. 18A, positioned in the interior center of the housing 90 are center vertical dividers 93 separating the housing interior into at least two sections, a left housing section associated with a left center divider 93, and a right housing section associated with right center divider 93. In the embodiment shown, a removable cassette 50 (see FIG. 3A) can be inserted into each housing section. Two housings may be mounted on the cart, an upper housing 90 and a lower housing 95, such as shown in FIG. 1A.

Figure 20:
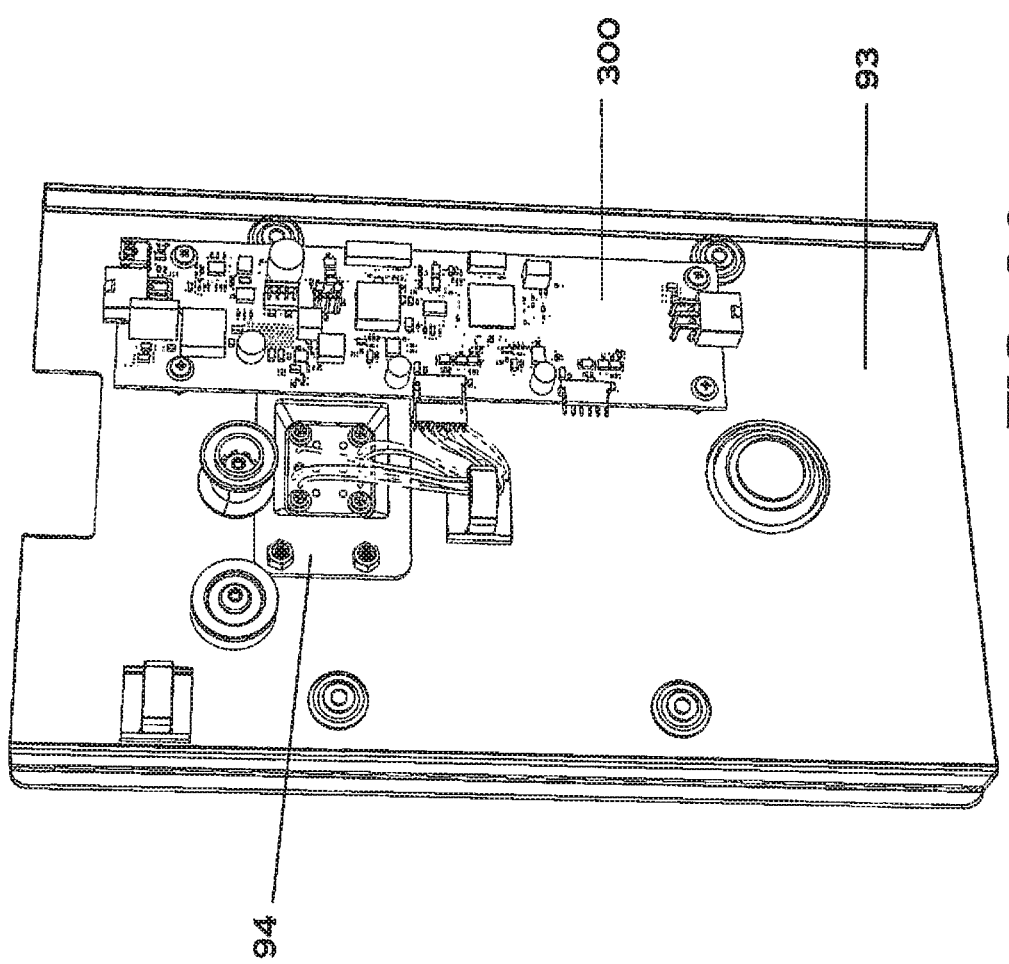
FIG. 20 is a rear perspective view of one embodiment of the center partition of a housing.

In a preferred embodiment, the chassis of the cart has a telescoping height adjustable support column 9, and with a telescoping support column, the upper housing 90 is generally mounted to the underside of the work surface 11 to avoid interference with the movement of the telescoping arm 9. In this embodiment, shown in FIG. 1A, a lower housing 95 is preferably mounted to the underside of the upper housing 90. With two housings, the cart 10 is able to accommodate four cassettes 50, next described. Power and communications to the lower cassette housing 95 is provided by a wiring harness that may be coupled to the housing wiring harness in the first or upper cassette housing 90. Instead of a daisy chained bus system, a linear bus could be used where each housing represents a separate node on a bus system, and each receives all housing communications but only responds to communications addressed to that particular housing. Each housing 90 (upper or lower), and housing sections (right or left) are addressable on the communications bus, and the address is imbedded in instructions/commands/queries and is interpreted in microcontroller firmware mounted on a printed circuit board (PCB) 300 positioned on a center divider 93 for each respective housing 95 and 90. (See FIG. 20). This micro-controlled firmware, in conjunction with the system software contained in or accessible on the system processor 30 and microcontroller firmware located in the cassette (such as on a cassette PCB), will direct instructions and commands from the user, via the system processor, to the proper housing, via a common power and communications bus (such as wiring harness or harnesses, and from the housing to the proper cassette and cassette component, as later described.

Figure 2C:
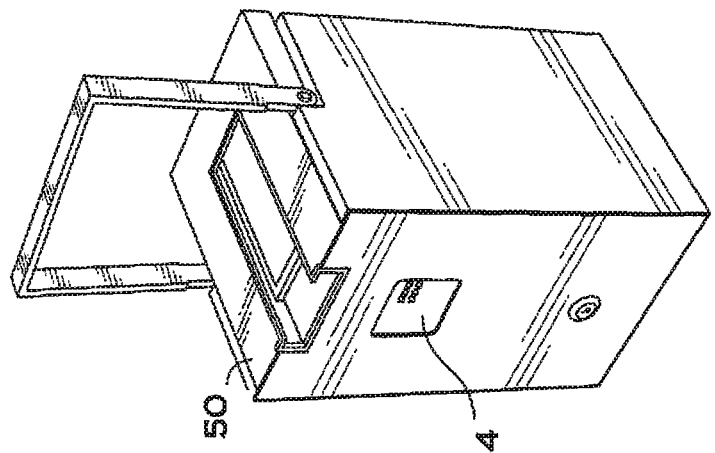
FIG. 2C is a rear perspective view of one embodiment of a cassette.
Figure 2B:
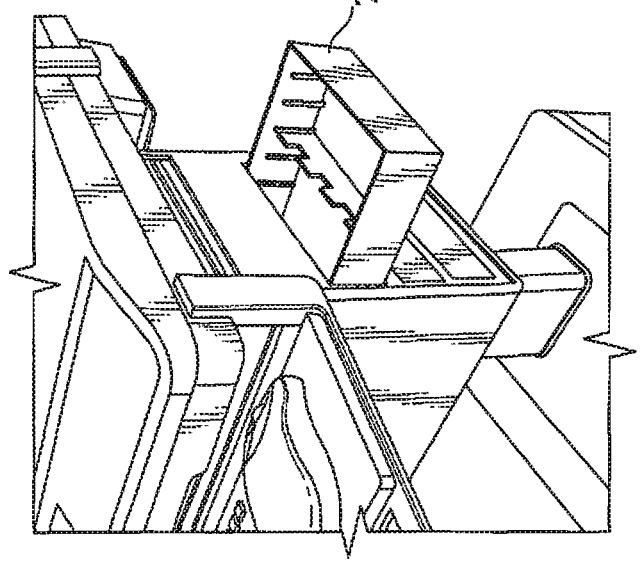
FIG. 2B is a detailed perspective view of one embodiment of the dispensing station depicting a drawer in a fully opened position.

Communications from the cassette housing 90, 95 to the cassettes is provided through the center dividers 93 in each housing 90, 95. Each center divider 93 includes an electronic interface device 94 that is coupled to the power and communications bus, and each interface device 94 will couple or interface with a cassette electronic interface device 64 on the rear of a cassette 50 (see FIG. 2C). In the embodiment shown in FIG. 5, the housing electronic interface device 93 is a six prong male connector, and the cassette interface device 64 is a corresponding inter-mating female plug (see FIG. 2C). The housing electrical interface device 94 is coupled to a housing wiring harness (not shown) that interfaces the housing firmware on the PCB 300. An additional wiring harness couples the firmware to a plug at the top of the housing 90 (see FIG. 20) for connection to the cart's computer system and cart power supply.

These wiring harnesses, as a common communications and power bus, will supply power and control/communications from the station's battery and processor, to the components and equipment located in the individual cassettes 50. The system is thus able to route communications to the appropriate component by using an address scheme for each component (as interpreted by the firmware in the cassette, if present). If cassette firmware is used, the firmware may have an internal database of the components positioned on the cassette board, and these components may be associated, at the cassette board level, with a drawer identifier or drawer location. The firmware may also have access to a modifiable memory table on the PCB to store a local map or image of the drawer identities and associated positions in the cassette that can be filled in response to a read ID command). The overall equipment configuration (and equipment addresses) for each cassette is preferably maintained, or partially maintained, in a system database, which may be stored in local memory for use by the system processor or in a remote server memory, or in both locations.

Figure 3C:
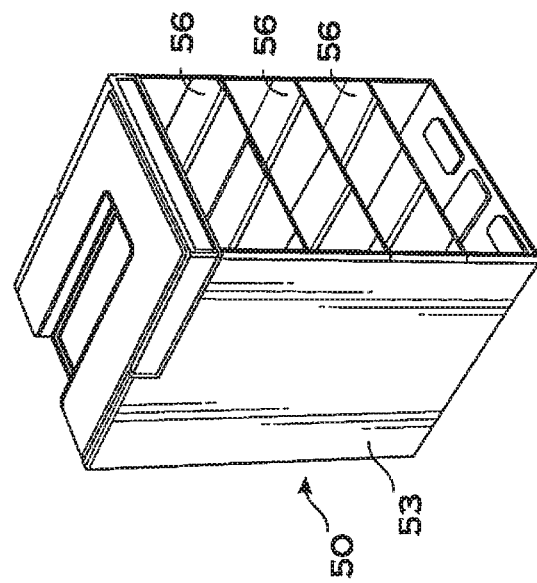
FIG. 3C is a front perspective view of the embodiment of the cassette in FIG. 3B with the drawers removed.
Figure 3B:
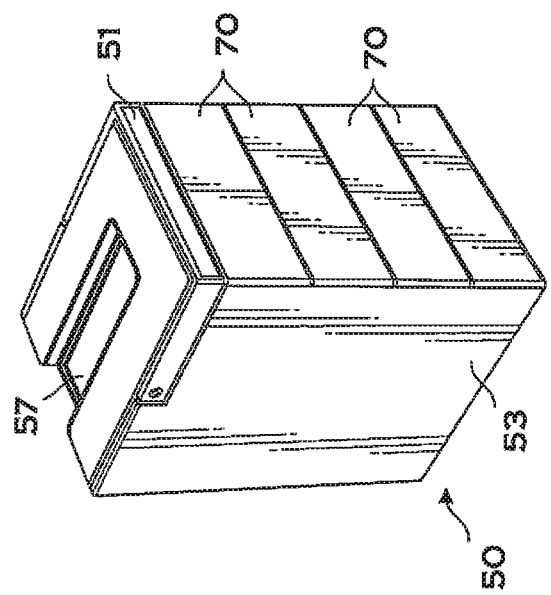
FIG. 3B is a front perspective view of one embodiment of a cassette with a handle closed.
Figure 3A:
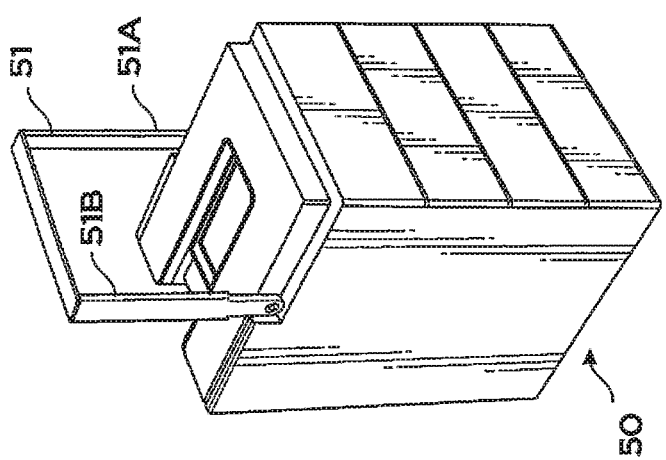
FIG. 3A is a front perspective view of one embodiment of a cassette with a handle open or deployed and pivoted upwardly.

One embodiment of the cassette 50 is shown in FIGS. 3A-3C. As shown in FIG. 3C, the cassette 50 is a six sided hollow rectangular frame 53 with one open side, into which a number of drawers 70 may be slidably positioned in the interior of the frame 53. The cassette frame 53 shown in FIG. 3C is closed on five sides (rear, top, bottom, side 1 and side 2) and open in the front. As shown in FIG. 3C, the cassette frame 53 has three horizontal dividers 56 that separate the interior of the cassette frame 53 into four separate spaces, each space containing two compartments (two compartments per divided space, for a total of eight compartments per cassette). These horizontal dividers 56 slide in slits on the frame 53 interior side walls, and can be repositioned on the frame 53 to allow customization of the drawer configuration of the cassette 50 to accommodate 2-8 drawers 70 in each cassette. The top facing surface of each divider 56 may have one or more shoulders or channels to interface a comparable channel or shoulder on a drawer bottom, to act as a drawer guide.

Figure 9:
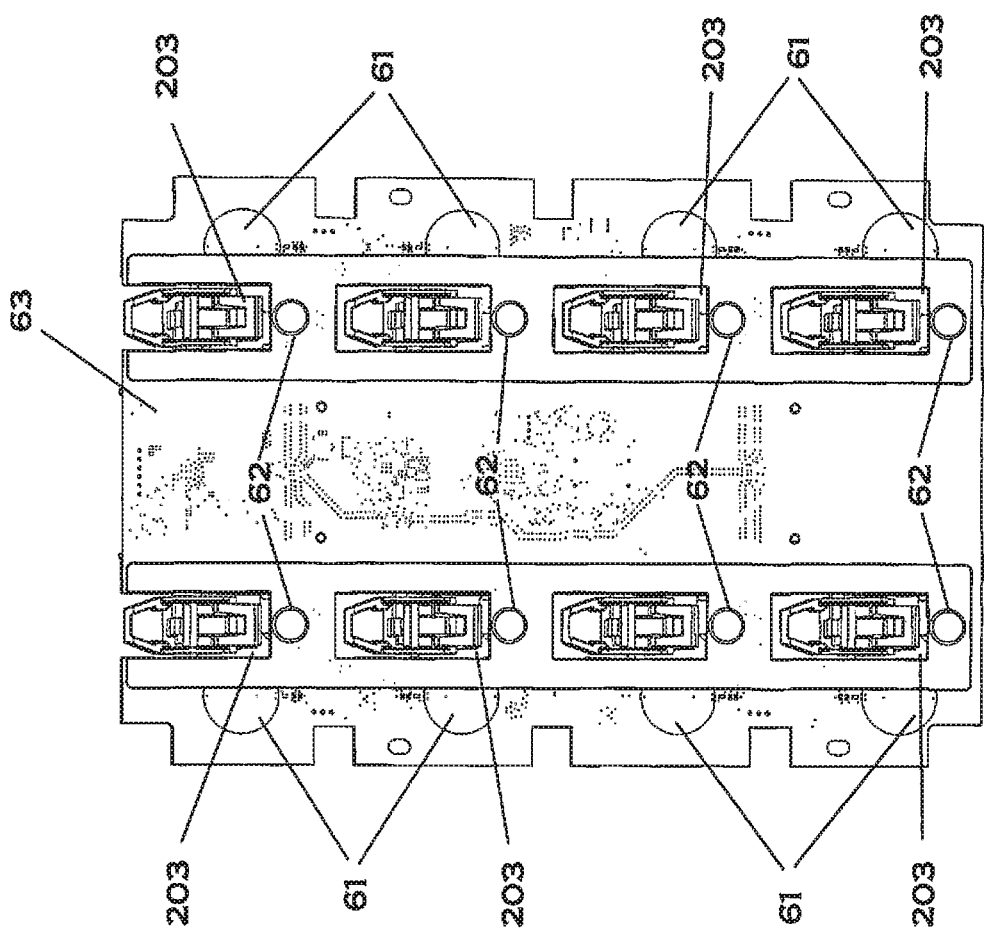
FIG. 9 is a front elevation view of one embodiment of the cassette rear partition.
Figure 10:
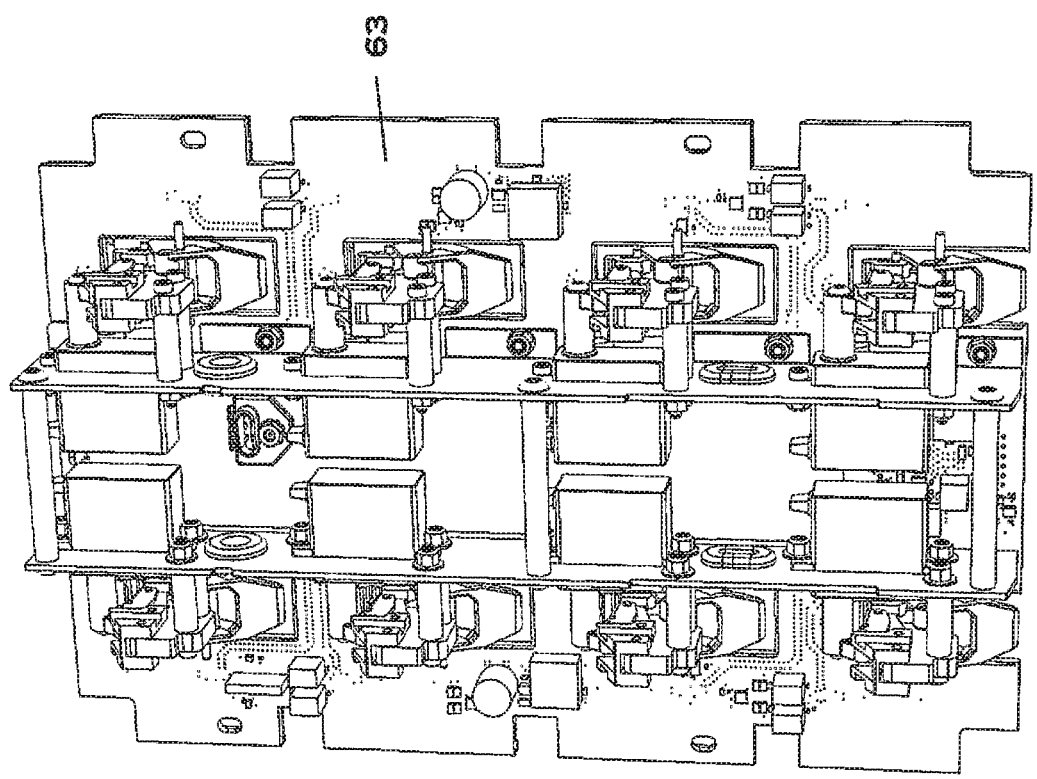
FIG. 10 is a rear elevation view of one embodiment of the cassette rear partition.

Located in the interior rear of the cassette frame 53, is a rear vertical partition 63, on which equipment may be mounted (see FIG. 5). For instance, mounted on this partition 63 are a series of actuators 200 and actuator latches 201. In a preferred embodiment, each compartment is associated with one actuator 200 and associated actuator latch 201. The rear panel of the cassette frame 53 is removably attached to the body of the frame to allow user access to the drawer actuators 200, actuator latches 201, and drawer sensors positioned on the rear vertical partition 63. As shown in FIG. 9, the front terminating end 203 of an actuator latch 201 is U-shaped, with the open end of the U-shape upwardly facing, but other shapes could be used.

Figure 4A:
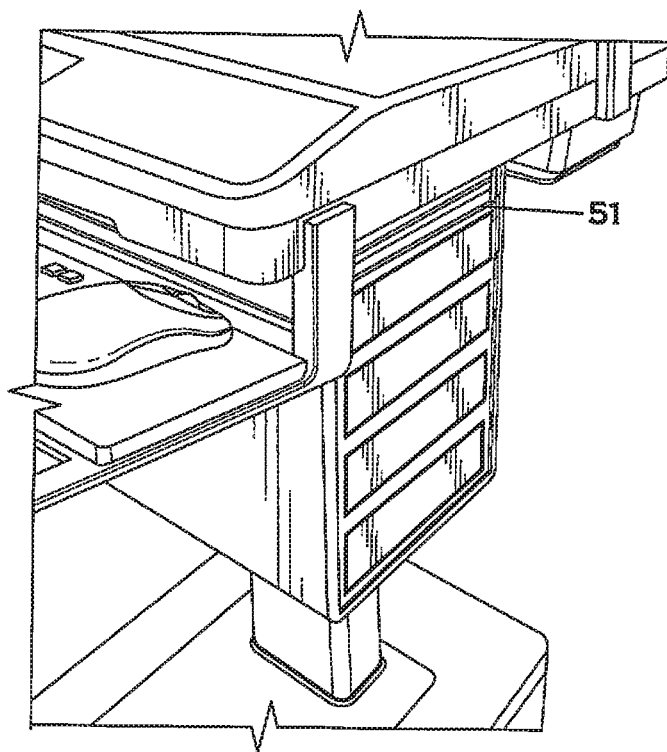
FIG. 4A is a detailed perspective side view of one embodiment of a cassette mounted in a housing with the cassette handle closed.
Figure 4B:
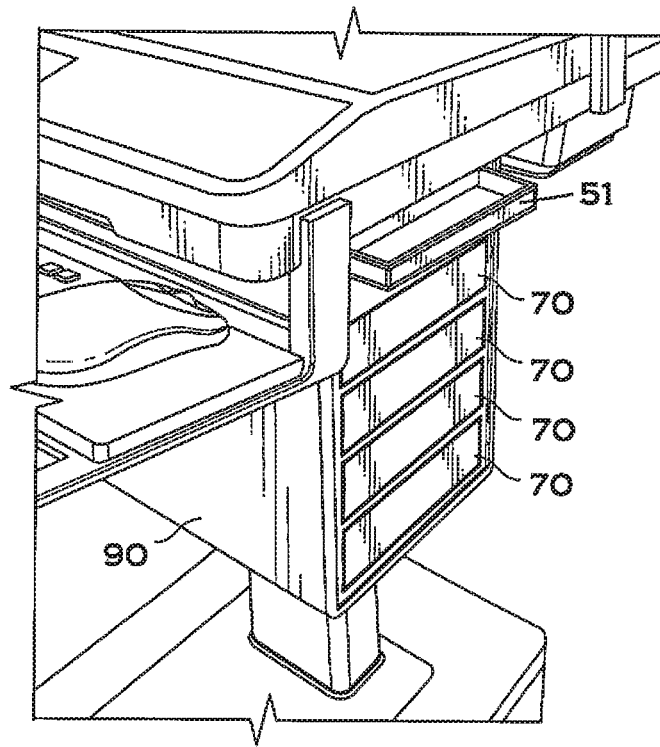
FIG. 4B is a detailed perspective side view of FIG. 4A with the cassette handle ejected or deployed.
Figure 18B:
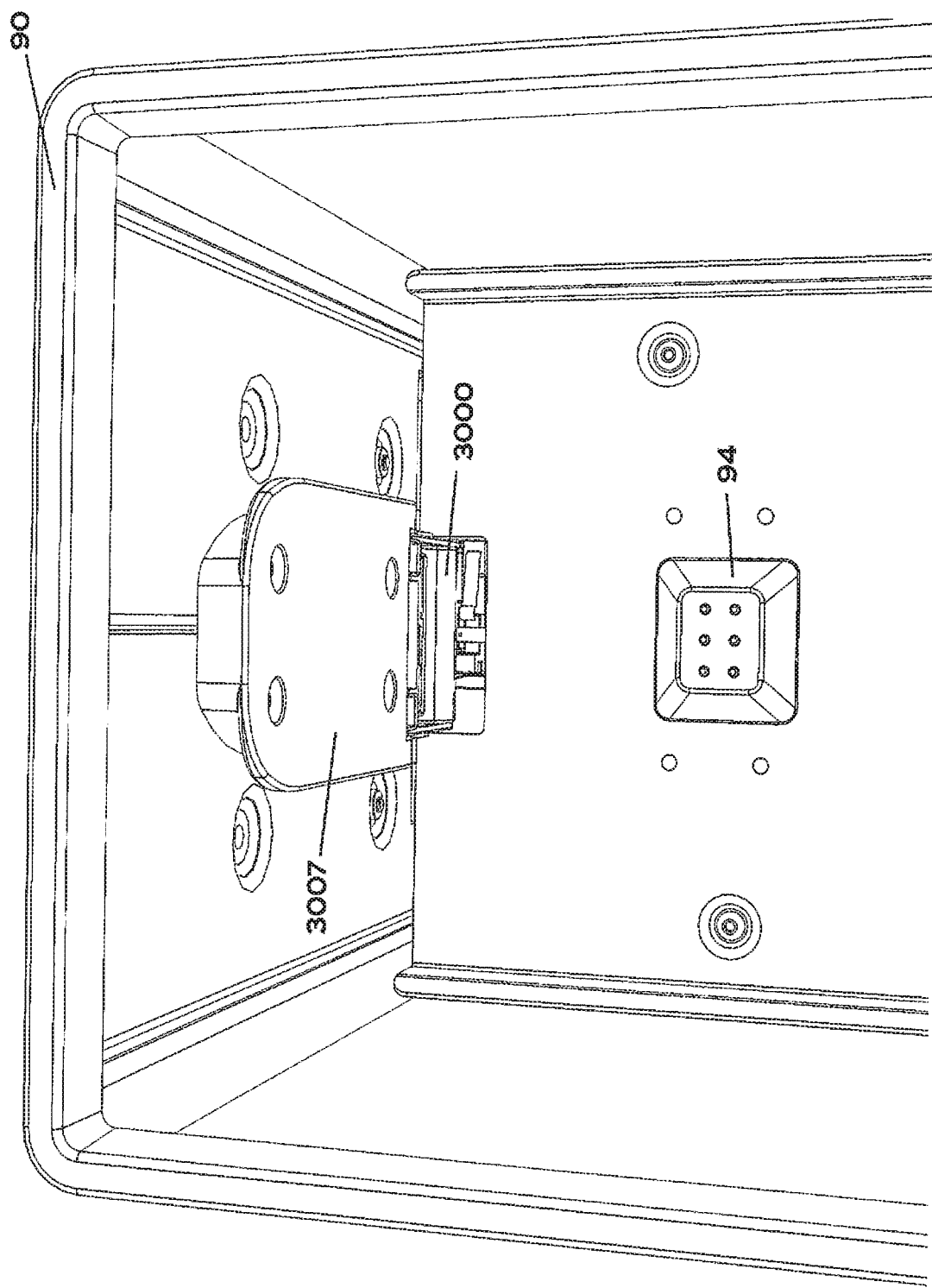
FIG. 18B is a detailed view of the housing of FIG. 18A depicting the cassette handle actuator.
Figure 19A:
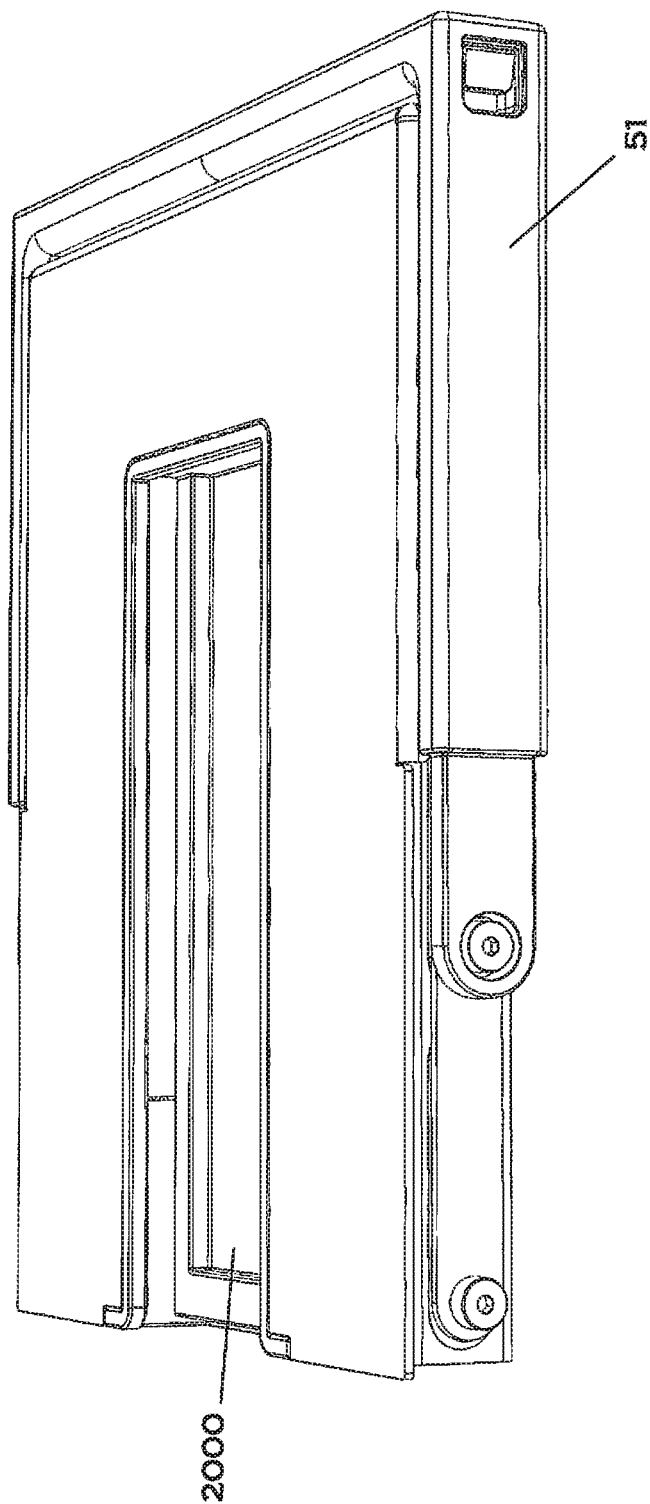
FIG. 19A is a perspective view of one embodiment of an actuatable cassette handle.
Figure 19B:
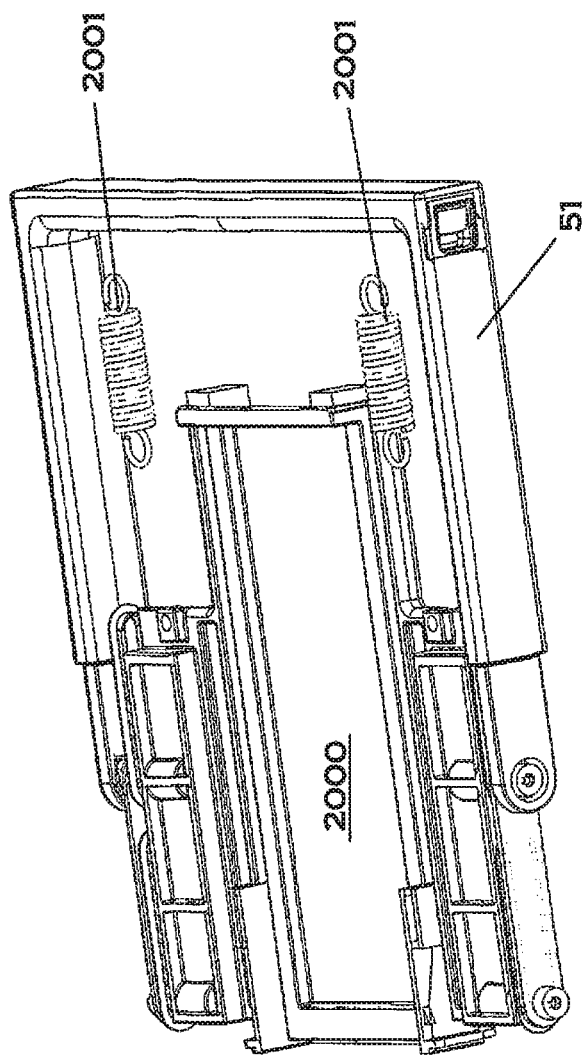
FIG. 19B is a perspective view of the handle of FIG. 19A with the top cover removed.

Coupled to the top front surface of the frame 53 is a spring loaded U-shaped handle 51 (see FIGS. 3A and 3B and 5). The handle 51 is pivotably mounted to the top of the frame 53. Note that the handle 51 is flush with the frame 53 sides and frame front. The handle 51, in a retracted or closed position, cannot be grasped by an operator, that is, the handle is inaccessible in the closed position (see FIG. 4A). Consequently, the cassette 53 cannot be removed from the housing 90 until the handle is electronically unlatched/ejected by a user. The handle 51 is pivotally connected to a slidable spring loaded latching plate 2000 (see FIGS. 19A and 19B), and this plate 2000 is latched in place with latch members 3000 positioned on the upper interior of the housing 90. See FIG. 18B. As shown in FIG. 18C, the latch member 3000 is a dual actuatable latch member having a left latch 3001 and a right latch 3002, separately actuatable. The left latch member 3001 will latch and lock to the slidable plate 2000 on the left cassette 50, and the right latch member 3002 will latch and lock to the slidable plate 2000 in the right cassette 50. When latched and locked, the handle 51 is in the retracted position (flush with the cassette drawers). To eject a handle 51 to a released or deployed position, as shown in FIG. 4B, the user will activate an eject command from the input device. This command will activate the servo or solenoid or other actuator associated with the selected cassette, to activate the appropriate left or right latch 3001 or 3002. On actuation, the latch 3001 or 3002, will disengage from the sliding handle plate 2000, allowing the plate 2000 and attached handle 51 to slide forward by action of springs 2001, which deploys the handle to a position where the handle extends past the front of the cassette frame 53 and allows a user to grasp the handle 51, as shown in FIG. 4B. One sequence of steps to eject a cassette handle, in one version of the station (the Medlink lite version), is shown in the table of FIG. 15A. Another sequence of steps to eject a cassette handle in another version of the station (the Medlink Pro version) is shown in the table of FIG. 15B. To reposition the handle 51 in the closed state, the handle 51 is pushed inwardly until it is flush with the cassette front surface, where the handle latch will reengage the sliding plate 2000. When a cassette 50 is installed in a housing 90, the user may also deploy the handle 51 manually in the event of a power failure, by inserting a key in the housing, which turns a linkage to manually move the latch actuators to a released position. Switches in the housing (in electrical communicating with the processor) may be associated with each cassette, and the switch state can be used as an indicator of the presence or absence of a cassette.

Figure 4C:
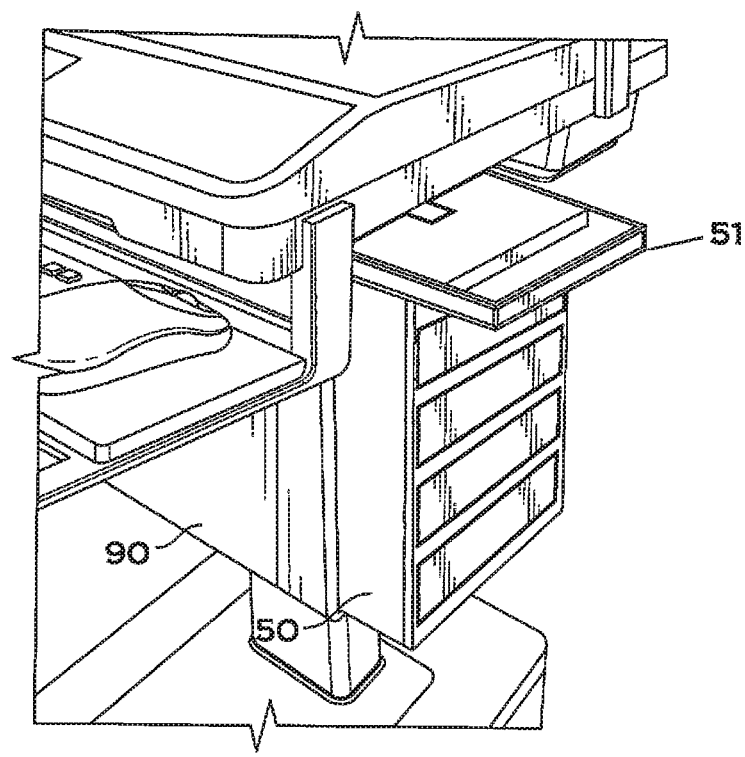
FIG. 4C is a detailed perspective side view of FIG. 4B with the cassette partially removed from the housing.
Figure 4D:
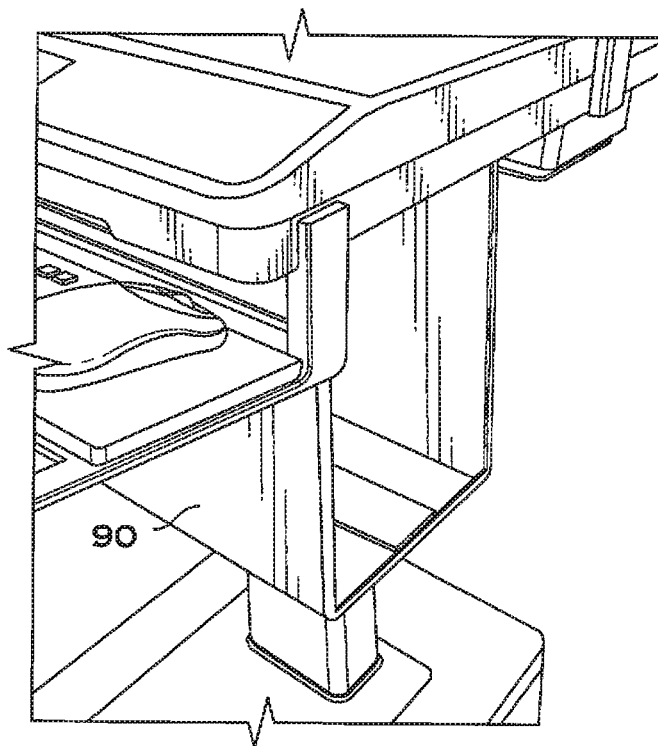
FIG. 4D is a detailed perspective side view of FIG. 4A with the cassette removed from the station.

Once the handle 51 has been deployed, the user can grasp and pull the handle 51, sliding the cassette 50 toward the user and out of the housing 90 (see FIGS. 4C and 4D). The handle 51 may then be used to transport the cassette 50, as the handle 51 is pivotably attached to the frame 53 and sliding plate (see FIG. 3A). In the embodiment shown, the handle 51 may not be repositioned into the retracted position once the cassette 50 is removed from the housing 90, as the locking latches 3001 and 3002 are located in the housing 90.

As shown in FIG. 3B, the top exterior facing portion of the cassette frame 50 has a channel 57 defined therein, which is shaped to slidably inter-mate with a downwardly facing shoulder 3007 in the interior of the housing 90, for sliding the frame 53 into the cassette housing 90 to allow the latch actuators 3000 to interact with the slidable plates 2000 (see FIG. 18B).

Since the cassette 50 connects into the center divider 93 of the housing 90, communications/control and power is provided from the cart 10, through the housing 90 to the vertical partition 63 in the cassette 50. The wiring harness from the cassette plug 64 on the rear of the cassette 50 is attached to a PCB (printed circuit board), and from this board, wires connect to the separate components mounted on this rear partition 63 in the cassette 50. Communications and control of the components are accounted for by microcontrolled firmware. This firmware may be mounted on the PCB in the housing center divider 930, in the cassette rear partition 63, or both. In one embodiment, the addressable command from the processor is passed to the firmware in the housing located on a housing printed circuit board, which, if addressed to a cassette in the housing, will pass the command to the appropriate cassette (the housing firmware may strip off the cassette address, leaving the component address (such as actuator address 0-31), and the firmware in the cassette located on the cassette printed circuit board will respond to the command with the appropriate response) (such as actuate activator 16, or read RFID 00), and communicate status of the command (if needed, such as respond with RFID tag value) back to the housing, which passes the response to the processor. The system has distributed intelligence with high level user interface functionality located in the cart processor, and the component level interface functionality located in firmware in the housing and the cassette. The cassette microcontroller firmware is used to route power and communications signals from the common power and communications bus via the six wire plug (two wires for power, two wires for addressable communications, and two wires used to differentiate the upper housing from the lower housing), for distribution of actions or commands to the equipment on the rear partition 63 of a cassette (such as actuators, proximity sensors, RFID reader and antennas). The firmware on the housing 90 will direct communications to the proper cassette 50 (right or left) based on the addresses provided in the instructions from the system processor. The processor can access the drawer location which is stored on computer memory, where the computer memory is either located on the cart or remotely located, such as on a system server (in a client/server relationship where the cart processor is the client in communication with and a remote server computer) with drawer information stored on the server computer memory). In many embodiments, the computer memory includes a database which generally has stored drawer identifiers, which may include drawer size/drawer location in the cassette interior, where drawer location can be specified in a variety of different ways, such as by specifying a compartment(s), or other associated locations, such as actuator locations (e.g., actuator address 0-15), sensor address, or other addresses or locations associated with a compartment or with the drawer. The database with the configuration map may contain RFID tag or the unique drawer identifier information (such as on the Medlink Pro version, described later), and associate each RFID information with all other patient identifiers assigned to the particular drawer, which information can be stored in computer memory located remote for the cart, such as in a server computer, the hospital HIS system computer memory). In this client/server embodiment (the client being the cart processor and the server being a remotely located computer system with access to computer memory), the server system is accessed with either a wireless or a wired communication channel. The system will use this configuration map or database for routing instructions and control signals, based on input from a user (e.g., open drawer A5). The firmware on the cassette will decode the instruction from the processor/housing and route the instruction to the final destination, to the appropriate equipment on the cassette partition for action or communication (e.g., power actuator 8, for instance, or query status of proximity sensor 3).

The following is one embodiment of an address scheme for use in the system to address housings, cassettes, and drawer positions:

Each housing assembly has a left and a right cassette of drawers (left and right from viewpoint of T7 operator).
Within a cassette, the drawer compartments are numbered, by rows, starting from the upper left position: (0, 1), (2, 3), (4, 5), (6, 7).
The base address of a left cassette is 0.
The base address of a right cassette is 8.
The base address of the upper housing is 0.
The base address of the lower housing is 16.
The absolute address of a drawer position is: housing base address+cassette base address+drawer position number.
The absolute address of a cassette is: housing base address+cassette base address.
Each component (latch actuators, electronic reading devices, and proximity sensors, switches) is also addressable (e.g., such as 0-31). The specific type equipment addressed may not be specified in the command, as the instruction can inform the cassette firmware of the equipment addressed (e.g., an open command is addressed to actuators; a read ID command is addressed to RFID sensors, etc.).

Figure 6A:
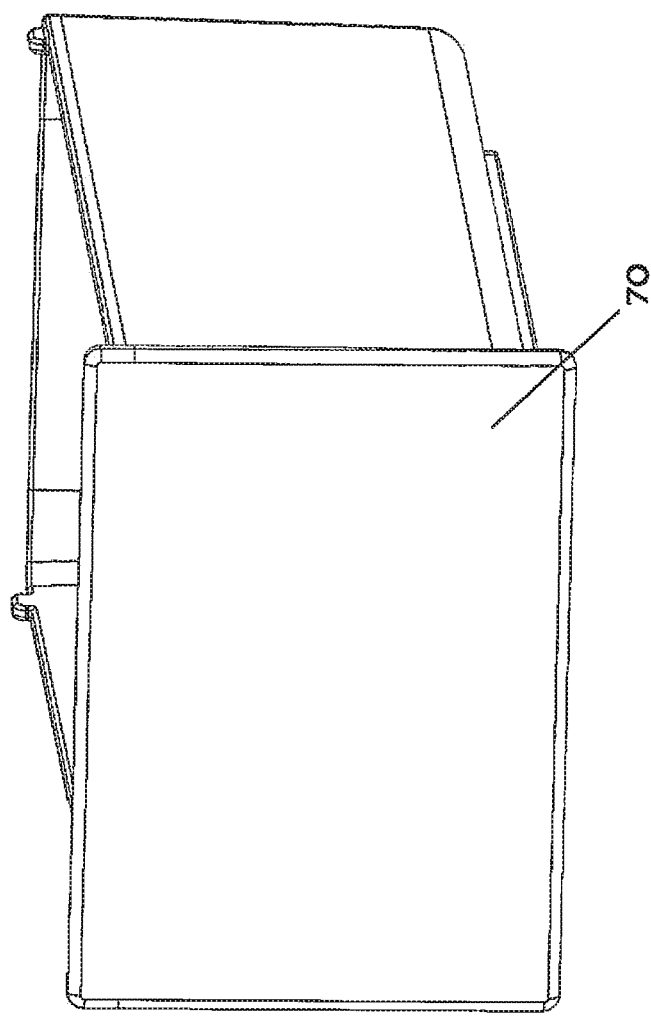
FIG. 6A is a perspective front view of a small drawer.
Figure 6B:
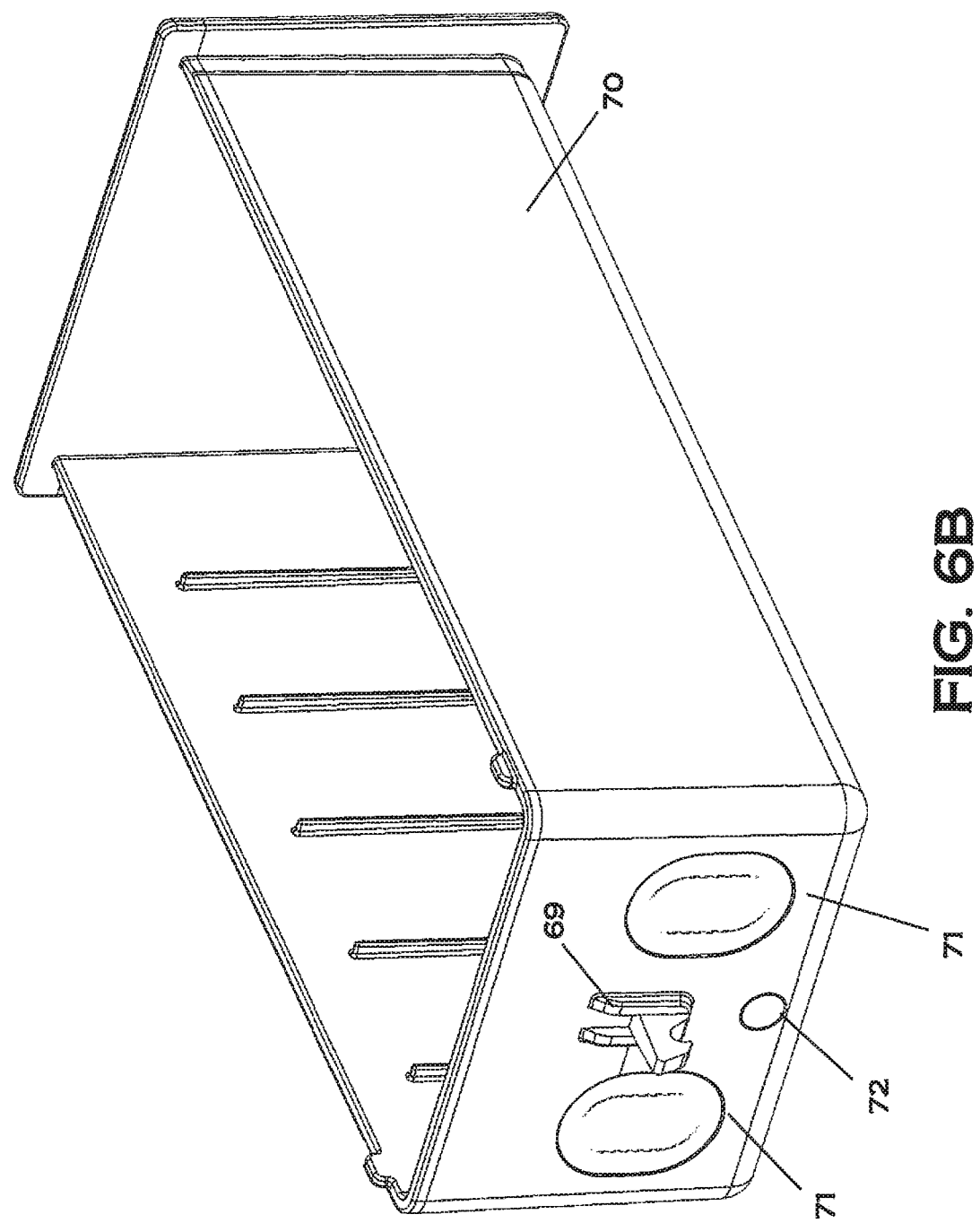
FIG. 6B is a perspective rear view of a small drawer.

Drawers 70 are slidably positioned in one or more drawer compartments in the interior of the frame 53. In a preferred embodiment, drawers 70 are available in three sizes, a small drawer that occupies a single cassette compartment, a medium drawer that occupies two side-by-side cassette compartments, and a large drawer that occupies four cassette contiguous compartments (two side-by-side compartments one on top of the other). One embodiment of a single drawer is shown in FIGS. 6A and 6B. As shown, the front of the drawer 70 lacks drawer handles or a grip or graspable feature, and when closed, the drawer front surface is flush with the outer frame of the cassette. Consequently, when closed, a drawer 70 cannot be opened unless unlocked and ejected or opened by the system, as later described. Each drawer 70 is a rectangular enclosure with an open top. Preferably, located on the back or rear exterior portion of each drawer 70 (see FIGS. 6B, 7 and 8) are sensors or sensor targets, including a proximity sensor target 72 (here a permanent magnet to interact with a magnetic proximity sensor) and an electronically readable drawer identifier tag 71. In one embodiment, the readable identifier tag is a passive RFID tag containing an ID which is used to uniquely identify the drawer, and to also identify drawer size, (such as by having the first readable alphanumeric character in the stored tag identifier specify drawer size). One type of proximity sensors are actuatable switches c (such as two position switches), mounted preferably in the cassette frame, one per compartment. In a switch embodiment, the "proximity sensor target" 72 can be the drawer back. As shown in FIG. 6B, a single small drawer includes two RFID tags 71 but a single proximity sensor target (magnet) 72. As a half drawer can be located in the right side (adjacent to the rear of the cart) or left side (adjacent to the front of the cart). By placing RFID tags 71 on each rear side of the half drawer, a half drawer is not sensitive to whether it is positioned in the front or rear portion of the cassette.

When a drawer 70 is installed and closed in a cassette frame 53, the rear of the drawer faces the front facing portion of the cassette rear partition 63. Located on the front facing portion of the partition 63 are a series of proximity sensors 62 (such as a hall effect sensor or reed magnetic proximity sensors), with preferably one sensor per compartment, and a series of reading devices 61 to read the drawer electronic readable identifier (also with at least one device 61 per compartment). In the embodiment shown, the reading devices 61 are RFID antennas 61, each positioned to interface and read an RFID tag 71 on a closed drawer 70. The antennas are used in conjunction with a RFID interrogation device, such as located on the cassette PCB board e.g., using a common interrogation device to interrogate a RFID tag via the associated antenna. In other embodiments, each antenna could be associated with a separate RFID interrogation device. The devices 61 and proximity sensors 62 communicate status with the system processor via the communications bus and firmware on the cassette and on the housing.

Figure 7:
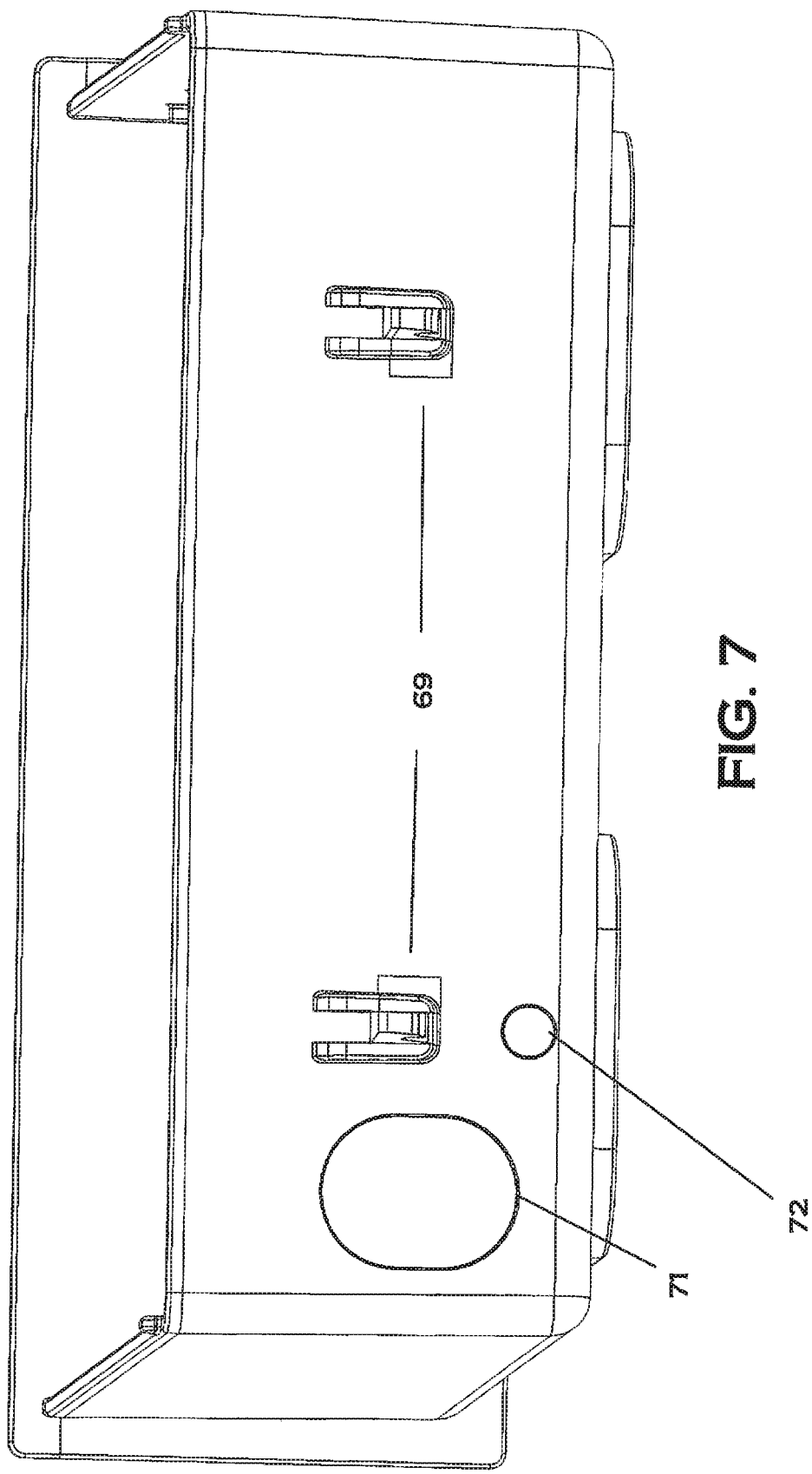
FIG. 7 is a perspective rear view of a medium drawer.
Figure 8:
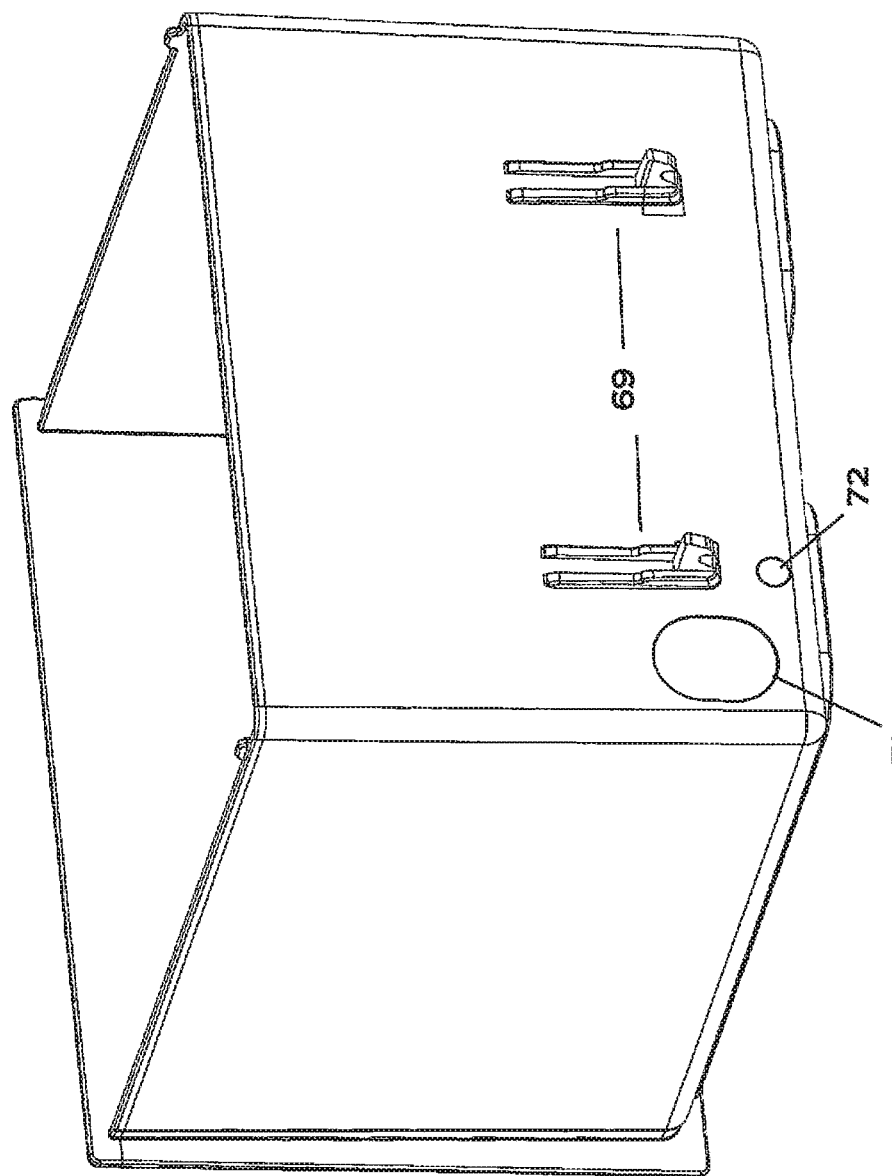
FIG. 8 is a perspective rear view of a large drawer.

Each drawer 70 preferably also has at least one latch 69 extending outwardly from the drawer's rear exterior surface, that will couple with corresponding actuator latches 201 on the interior partition 63 of the cassette, as later described. As shown in FIGS. 6B, 7 and 8, a preferred drawer latch is a downwardly shaped hooked latch, that will inter-mate with the "U" shaped actuator latch 201 on the rear partition 63, for closing and opening a drawer. As the drawers 70 lack handles or a graspable surface, a drawer 70 can be opened only by action of the cart processor 30 or by manual override, later described). To open a drawer 70, the operator will select a drawer 70 to open (the selection process is later described) via one of the cart's input devices. The open command is used to actuate or power one or more actuators 200 (generally a servo) associated with the drawer to be opened on the cassette partition 63, which results in a movement of the associated actuator latches 201 that are coupled to the actuators 200. In one embodiment, a user enters the open command with a drawer label identifier (which can be patient identifier, drawer location, or other identifier), and the processor places the drawer open command on the communications bus. Each housing receives the command, and determines if it is directed to a cassette in that housing. The proper housing (via firmware on the housing PCB) will forward a possibly modify command to the proper cassette. The cassette (via firmware located on the cassette PCB) will interpret the command, and activate the appropriate latches to open the proper drawer. In a preferred embodiment, actuator's (servo motors) move the associated actuator latch 201 first forward, toward the drawer 70, then downward, toward the floor. The path the actuator latch 201 follows during actuation can be controlled by a shape of the linkage connecting the actuator latch to the actuator, or the linkage can be guided by a shaped structure (such as a channel), or the actuator servo itself may have a shaft that follows an eccentric path, suitably moving the linkage coupled to the servo shaft. In one embodiment, the actuator 200 may communicate its status to a servo manager, (as open, closed, in motion), such as to the firmware, for use by the system computer on interrogation.

Figure 2A:
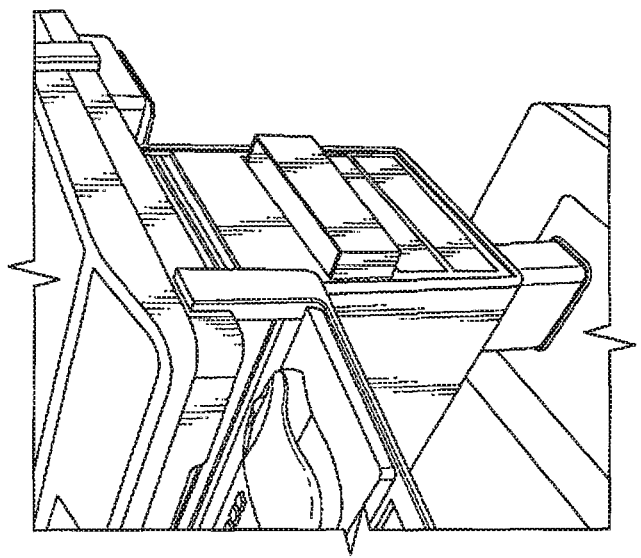
FIG. 2A is a detailed perspective view of one embodiment of the dispensing station depicting a drawer in the almost closed position.

As the actuator latch 201 moves forward towards the drawer 70, it remains engaged with the drawer latch 61, thereby pushing the drawer 70 slightly forward with the forward motion of the actuator latch 201. The final downward movement of the actuator latch 201 allows the actuator latch 201 to disengage from the drawer latch, that is, the actuator latch "U" shaped hook clears the downward hook portion of the drawer latch 69, thereby separating the latches and unlocking the drawer, allowing the drawer 70 to be opened by a user. This open action of the actuator latches places the drawer 70 front slightly beyond the front edge of the corresponding cassette frame 53, such as shown in FIG. 2A. This position of a drawer 70 is termed "almost closed." In this almost closed position, drawer 70 is unlatched from the actuator but within such proximity to the actuator that the actuator can retract the actuator, reengage the latches and close the drawer. In the almost closed position, an operator can grasp the drawer front top edge and slide the drawer fully opened to access the drawer interior. The drawers are slidably positioned or mounted in the cassette frame 53. An opened drawer 70 is considered any position of the drawer 70 past almost closed position, providing access to the drawer interior. Until the drawer reaches the almost closed position, it cannot be opened, as the drawer is locked, that is, the cassette latch and drawer latch are inter-mated. Medium and large drawers have two drawer latches (such as shown in FIGS. 7 and 8), and consequently, the system must activate two actuator latches simultaneously to unlock and open these size drawers. Hence, the cart must "know" the size of the drawers (which may be contained in the configuration map in the computer memory or in memory on the cassette PCB) to allow proper control for opening, closing and locating the sensors that interface with the drawer 70.

Figure 14:
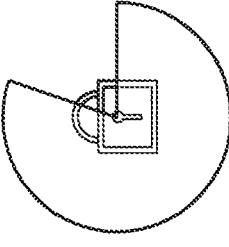
FIG. 14 is a screenshot depicting monitoring drawer open status.

In some embodiments, once a drawer 70 is unlocked and positioned in the almost closed position, the system processor 30 can monitor the period of time the drawer remains in the unlocked almost closed position, and if a predetermined time is met, the system can reverse the actuator latch 201 (e.g., the servo reverses) to close the drawer 70. As shown in the screen shot of FIG. 14, the drawer 70 assigned to "Richard Robin" (a patient identifier) has been opened, and the system is tracking the amount of time until the drawer will be automatically closed. To close, the actuator latch 201 will retrace its path, first moving upwardly to reengage the drawer latch 69, then moving in a rearward direction, thereby pulling the almost closed drawer into fully closed and locked configuration; that is, the system automatically closes a drawer. The system processor knows when a drawer has been opened (by tracking the command status, or by the proximity sensors). For instance, the proximity sensor can relay status such as "closed" (the drawer is flush with the cassette frame and locked by the actuator), "open" (the drawer is out of range of the proximity sensor) or almost closed as defined herein). Hence the system processor can detect how long a drawer 70 is in the almost closed position, by, for instance, polling the status of the proximity, which status may be stored on the PCB board, or directly queried based on the poll instruction. In one embodiment, the proximity sensors are used to detect drawer open, closed and almost closed position. One sequence of steps to open and close a drawer in one version of the station (the Medlink lite version) is shown in the table of FIG. 16A. Another sequence of steps to open and close a drawer in a version of the station (the Medlink Pro version) is shown in the table of FIG. 16B

In operation, the system "knows" the identity, size and location of every drawer in the cart. In one embodiment, each drawer has at least one unique identifier established in the RFID tag 71, and that tag is readable by an RFID reader/antenna 61 positioned on the cassette rear partition 63. When the drawer 70 is closed, the RFID antenna 61 is positioned adjacent to the drawer RFID tag 71, allowing the RFID reader to interrogate the RFID tag 71, receive the stored information and communicate the stored information to the system processor for use. Each RFID reader or antenna 61 has a unique location on a cassette 50, and can be electronically addressable by the system processor to initiate a query of the associated RFID tag. The system processor may request the RFID reader to query the RFID tag on a drawer. Once a RFID tag is read, the processor knows or can determine which drawer location(s) is associated with the tag that was read. Armed with this information, and the information on drawer size from the RFID tag, the system can determine the configuration of the drawers in the cassette (e.g., query each antenna for information, and map the responses). Consequently, the system (via the processor and software and computer memory) knows what drawers 70 are present in each cassette 50 in the cart 10, the specific location of each drawer 70 in each cassette 50, the size of the drawer 70, and in some embodiments, may have stored the RFID information or additional sensor or actuator addresses associated with each drawer in the cassette 50. The configuration of the station (number of housings, number of cassettes in each housing, and the identity of the drawers in each cassette, such as patient identifier) is preferably stored in the associated system memory (either local and/or remote on a server) as part of the database configuration map describing the station configuration. The station configuration can be displayed on the system display device (such as a GUI interface) as a visual map of the cart's cassettes, for use by an operator. In certain embodiments, the stored configuration information is limited, and consequently, the configuration map displayed will be limited.

At designated intervals or alternatively, on designated events (e.g., drawer closing), the system processor will interrogate or poll a drawer or the equipment to verify/update the system configuration. For instance, if a cassette has been removed, the system knows the cassette has been removed (from the ejection sequence, and in some embodiments, from a sensor reading (such as a switch output)). If a cassette has been recently installed, that event can trigger an interrogation sequence of all RFID antennas 61. In this event, the system processor can interrogate the newly installed cassette to determine the identity of the drawers in that cassette, and update the configuration map with the new drawer identifiers, sizes and locations. For instance, in a server embodiment, the system processor can determine the RFID tag information in an installed cassette, pass the RFID information to the server, and download the patient identifiers stored in the server to repopulate the configuration map to be displayed on the cart's display device. In a server embodiment, multiple stations may have drawer information stored on the server memory (and the server may also have a cart or cassette identifier stored and associated with each station/cassette). In this fashion, the system updates its configuration data to stay current.

Once a drawer 70 is fully opened, the system generally loses communication with the drawer 70, as the RFID tag 71 and magnet 72 are too remote from the RFID reader/antenna 61 and proximity sensor 62 for interaction with the associated sensors. On closing of a drawer 70, the system may confirm/update the identity of the drawer 70, and if a drawer 70 has been swapped out with another drawer 70, update the configuration map with the new drawer data and may download the associated patient identifiers from the server, or a HIS system, later described. The display device generally will indicate that the drawer is open when a drawer has been opened or removed, reflecting the status of the drawer. Preferably, if a patient drawer 70 is opened, the system will not allow a second patient drawer to be opened (absent, for instance, an override command, administrator access, or pharmacy access, for instance, where an "open all drawers" command may be utilized).

The control of the drawers is undertaken by users interacting with the system software via the system input devices. The system software generally provides for a "System Administrator" user, such as a supervising nurse, to log into the system and configure the system. In general, only one user may be logged into and controlling a station at any given time, however, the cart may be configured to accommodate multiple users, logged on at different times. Configuration of the system for multiple users is preferably undertaken by the System Administrator. Other configuration actions are preferably undertaken by the System Administrator, or another user that has been granted access to such actions by a System Administrator. For instance, when the cart is shared among users, specific configurations can be associated for each UserID, or groups of UserIDs, to customize cart operation according to each user or user group preferences. For instance, certain UserIDs may only be provided access to designated drawers having specific identifiers (such as ward identifiers), or only provided access to the system at designated locations. The System Administrator or other properly credentialed user, can provide different rights to the different users, or different groups of users, and store these access rights, or group rights, in system memory (generally local cart memory). Once logged in, a user may be denied access to certain cart functionality, such as denied access to certain drawers, denied the ability to eject cassettes, or denied other station functionality. For instance, a particular user group may be denied or granted rights to open all drawers at one time. The system, as described, is highly configurable.

Figure 13:
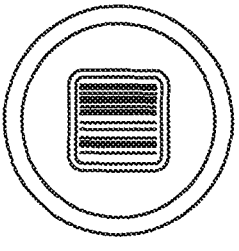
FIG. 13 is a screenshot depicting drawer assignment.

Additional information (patient identifiers) may be associated with specific drawers in system or server memory. For instance, a particular drawer may be assigned to a particular patient. To assign a patient identifier to a drawer 70, a properly credentialed user (granted the right to assign drawers) selects the drawer to assign (the user may first have to select the cassette on which the drawer is to be assigned in some versions), and then activate the assign function from the input device. See the screen shot of FIG. 13. The user may select a drawer by clicking on an image of a drawer, or touching an image from a touch screen input, or inputting a specified drawer identifier (such as A1, A2, A3, A4). By activating the assign command, the user can then input additional information to be associated with the drawer in the configuration map (and replace previously stored information), such as patient ID, patient DOB, ward location, patient bar code or hash code identifier, location identifier (e.g., patient room), location bar code or hash code identifier, or other pertinent information. In some embodiments, multiple patient identifiers can be associated with a particular drawer, such as patient ID, bar code, location, etc. Once stored, designated identified characteristics, such as patient name, can be displayed on the system display device. The information displayed, in some embodiments, can be controlled via system configuration by the System Administrator. These patient identifiers may be transmitted and stored on a local or remote memory (a server database).

Figure 12:
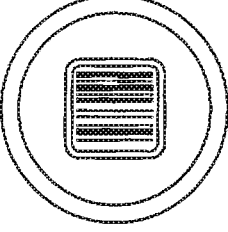
FIG. 12 is a screenshot depicting system configuration.

For instance, shown in the screenshot depicted in FIG. 12, is the configuration of a particular cart containing three cassettes. In one cassette, certain drawers (reference 124) are associated with specific patients, while one drawer is not assigned. In a second cassette, certain drawers (references 125) are associated with specific patients, one drawer is identified as a storage drawer, and one drawer is not assigned. In the third cassette, all drawers (references 126) are assigned to specific patients.

A drawer can also be assigned as a "common" supply drawer, where various supplies will be located that may be applicable to multiple patients on a given distribution workflow. From the assign/re-assign screen or command, stored drawer parameters can be edited, modified, or deleted, or a drawer de-assigned (wipe all identifiers) or reassigned. In some embodiments, to reassign a drawer, the system may require the user to have Administrator status. The complete set of patient identifiers associated with a specific drawer may also be viewed, for instance, via the assign command. Generally, the cassette components identified with a particular drawer (or the addresses of these components, such as actuators, and sensors) are generally not displayed for a user, as there is little need for such by the user—these identifiers are used by the station during station functions (open drawer, close drawers, interrogate status, etc.). One sequence of steps to assign a drawer for one version of the station (the Medlink Lite version) is shown in the table of FIG. 17A. One sequence of steps to assign a drawer in another version of the station (the Medlink Pro version) is shown in the table of FIG. 17B.

In some embodiments (the Lite embodiment, for instance, depicted in FIG. 11), the display device may display a picture of the current installed cassettes, and once a cassette is selected by the user, display drawer configurations for the selected cassette alone (such as using a zoom feature, to allow a user to zoom in or view only the information associated with the selected cassette and to interact with the selected cassette). This feature is useful if screen size on the display device is limited (for instance, in a wireless environment, a cart may be monitored remotely by, for instance, a ward nurse via a handheld tablet, or via an application on a smart phone). In a small screen display embodiment, displayed drawer information may be limited to drawer standard identifiers (without patient identifiers), such as drawer A1, or B2, such as where the letter (A, B, C, or D) reflects cassette identifier, and the number (1-8) reflects compartment identifier in the cassette). Alternatively, drawers may be displayed for selection by a list. Preferably, in most embodiments, the system's display output is configurable.

In other embodiments, patient data may be downloaded into the system memory from the hospitals information system (HIS) network (connected via a wireless connection between the system and HIS, for instance, similarly to the system in a client/server embodiment). To assign a drawer, the user selects a drawer, then requests a list of patients from the HIS, and the system displays the list received from the HIS on the cart display device. The user could select the patient to be assigned from the displayed list (e.g., mouse click on the selected patient, or touch the screen in a touch screen environment), and the system would then request the HIS to transmit certain of the patient's information (e.g., DOB, patient bracelet bar code; patient room, etc.). The system processor would receive the information and associate the patient information with the drawer and enter this information in the configuration map with the selected drawer (and, for instance retransmit the information to the server, if present). The cart can utilize the HL7 integration to access the patient-related information stored on HIS. Interfacing of the cart with the hospital's information system can be achieved using currently available software. Alternatively, the user could scan a patient's identifier, or enter a patient ID, and have the system query the HIS system (or server in some embodiment) for other patient information.

To open a drawer, the user selects the drawer to open (again, in some embodiments, select cassette first). The selection can be undertaken by various procedures, depending on the cart's configuration and the preferences of the particular user (UserID), the system capabilities, or configurations established at the work location. For instance, in one embodiment, the user scans the patient bar code bracelet with a bar code reader located on the cart (see, for instance the screenshot of FIG. 12). The scanned ID is then compared with stored information to see if a drawer on the cart has a matching patient ID associated. If so, the system would identify the drawer location in the cart, and actuate the actuator latches associated with the drawer location (accomplished in conjunction with the firmware on the system). This operation allows the selected drawer to move to the almost closed position to allow the user to grasp the front of the drawer and pull it fully open. Once opened, the nurse can interact with the drawer contents—load the drawer, remove prescriptions from the drawer, etc.

In other embodiments, the nurse may indicate which drawer to open, for instance selecting from a list displayed on the display device, or selecting from a displayed map of a cassette by touching the drawer on the displayed map of the cassette configuration, in a touch screen environment, or entering a drawer number (for instance "A8") in an input device. The input may be via keyboard, mouse, touch screen or other input device. Once the drawer is identified, the system, activates the actuators associated with the drawer, to unlock and move the drawer to the almost closed position.

In some embodiments, all drawers may be selected to be opened (or closed) at one time. The selection can be made on entry of a specific "open all" command, or, for instance, by entry of a specific location code (such as the pharmacy location code). In some embodiments, only drawers associated with a particular identifier may be opened at any given time, to provide for secure distribution of medication. For instance, all drawers for a given user group or patient could be opened at once for a common distribution at a nursing station.

In a preferred embodiment, if a particular patient's associated drawer is opened, another patient's drawers (e.g., assigned to a different patient) on the cart may not be opened concurrently. In other embodiments, a drawer identified as a common supply drawer may be opened while any other drawer is opened. In other embodiments, a supply drawer may be associated with a set of specific patients (or a subset of other drawers), and only opened when the associated patient's drawer is selected. As described, the system is flexible, allowing the user to configure a subset of drawers that can be opened concurrently, based on user supplied parameters.

As described, the drawers 70 in a cassette 50 can be opened from the cart processor. In other embodiments, the cassette 50 may be removed from a cart, and transported to a remote location and inserted into a remote cart or docking station (such as a fixed station located in the pharmacy area) for filling or emptying of the drawers. A docking station can be another cart, or fixed cart (not movable), where the cassette can be inserted into a housing 90. For a fixed docking station, the housing 90 may be dispensed with, and a simple communications plug, coupled to the cassettes' firmware to exercise control/communication with the cassette drawers, could be used. Preferably, the docking station has a display device and input device to display and/or modify the configuration of the docked cassette.

To close a drawer, different procedures can be used depending on system configuration and the equipment configuration. In some embodiments, the user may simply push the drawer back into the drawer slot until the actuator latch(es) 201 hook portion contacts the drawer latch(es) 69, and on further rearward movement rearward, two latches are positioned in an inter-mating latched relationship, thereby latching or locking the drawer in a closed position. In other embodiments, the operator may push the drawer 70 into the drawer slot until the drawer is in the almost closed configuration. Then the system processor, on detecting the drawer 70 (via proximity sensor 62), will (in conjunction with the firmware in the cassette) activate the actuators 200 associated with the drawer after a predetermined time (which can be set by the System Administrator), allowing the actuator latch 201 to pivot upwardly and re-engage the drawer latch 69, then pulling the drawer 70 into a closed, latched configuration. In other embodiments, the user may activate a close drawer command, possibly after selection (or before selection) of the drawer 70 to be closed, and the system would then cause the appropriate actuator(s) 200 to operate (for instance, in reverse) to allow the associated actuator latches 201 to re-engage latches 69 to close and lock the drawer. In other embodiments, the system may allow for a command to close all drawers, allowing activation of all actuators at substantially the same time (or two latches at a time to reduce the power draw on the system's battery).

In a preferred embodiment, the system software may interface with the hospital's information system (HIS) network. Generally, for this functionality, the cart's computer system will have wireless communication capability, but a hardwired interface with the processor can also be used (such as via Ethernet cable) to interface with the HIS. If the system includes a laptop, preferably the laptop has wireless capability. One benefit of interfacing with the HIS is that each cart 10 can exchange information with the HIS, similar to the exchange in a client/server embodiment. For instance, if a particular drawer 70 has been assigned to a particular patient, the patient information can be downloaded to the system from the HIS for population of the patient identifiers (DOB, Bracelet number, etc). Alternatively in some embodiments, drawer information can be communicated to the HIS and stored in the HIS system, such as cart identity or name, drawer identity (such as drawer unique RFID) and some of all patient identifiers. When the drawer is removed from one cart and positioned in a second cart, the second cart could query the HIS system for stored drawer assigned information (based on providing drawer RFID identifiers to the HIS and requesting transmission of associated patient identifiers), and receive the stored patient identifiers from the HIS. This allows drawers to be moved from cart to cart (or to a remote loading docking station) without the need to manually enter drawer assignments or drawer patient configurations. Once communication between a cart and the HIS is enabled, patient information can be shared between the cart and HIS using, for instance HL7 protocol. The sequence of steps in the table in FIG. 17B also depicts populating patient identifiers from remote computer memory, such as the server memory in a client/server embodiment of the station, or the HIS system memory.

The cart can also store cart or drawer activity, either in local memory, server memory, or in other embodiments, to transmit activity information to the HIS, in order to run reports of cart usage (user usage), drawer activity, and other relevant statistics. Reports may be compiled from the cart system, or in other embodiments, from the server or HIS with suitable software in the HIS and server. In one embodiment, once installed in the cart, the processor may inform the HIS of the drawer's present location, for tracking of the drawer history. The cart can utilize the HL7 protocol to access the patient-related information stored on the HIS. This interfacing of the cart with the hospital system can be achieved using currently available software.

The cart system includes manual overrides to allow a cassette to be removed or ejected, and for the drawers to be opened, for instance, in the event of a power failure. For instance, one manual override for a lockable cassette handle is to have the handle lock activated by a manual hardware key on the housing for manual removal of a cassette from a housing. A similar hardware key could also be used on the cassette, to manually unlatch all of the activator latches (via a linkage system coupled to the lock) to allow all drawers (e.g., manually actuate all eight activator latches) to open. For instance, manual activation may be needed in the event of a power failure, or when the cassette is transported outside of the housing and thus not in electrical communication with the cart.

On initial set up, the System Administrator sets up and configures each cart, that is, the administrator can initialize the data fields and configure the system as desired, set up the user ids/passwords, assign the cart an identity or reference code (if it is to network into the hospital system (e.g., client identifier for use in a client/server system)), establish user groups to control access to the drawers for refilling; identify and label drawer information fields to be associated with each drawer and RFID tag (patient bar code; room ID; DOB, etc.). The staff may also initialize the drawers by assigning patient values or identifiers to them, particularly when the system networks into the HIS, such as by choosing a patient to be assigned to a drawer, preferably from a list received from the HIS system, and receiving the patient identifiers (such as from the HIS system) and populating the appropriate data fields for display on the cart. The staff may identify some drawers as a common supply drawer; identify relevant location codes (pharmacy or ADC location, patient room code, etc.) as needed.

Once the cart/cassettes are set up and configured to associate a specific patient with one or more RFID tags (or other electronic identifier, such as a bar code) on the various drawers, the cart system can be used. The user takes the cart (or just the cassette) to the ADC, and can open all drawers in a cassette (possibly after scanning in the location code of the ADC or pharmacy) and the system may display a picture showing drawer locations and drawer identifiers, to allow the user to properly open and fill the drawers with medications as needed for each patient, and for the common supply drawer if one is assigned. Alternatively, the user can open each drawer individually and sequentially to fill the drawers using the configuration map displayed on the visual display device.

Once the cart is loaded, the user will move the cart to the first location on his/her distribution workflow route, and for each patient at that first location; open that patient's drawer (s) (such as by entering the patient ID or scanning the patient's wristband with bar code reader), distributing the proper drawer contents, and closing the drawer. The user then moves the cart to the next patient location for distribution. This process continues at the second location, and then repeats until all patients at a specific area (such as a ward) are served. The user will then move the cart to the next location, and repeat the process.

Figure 11:
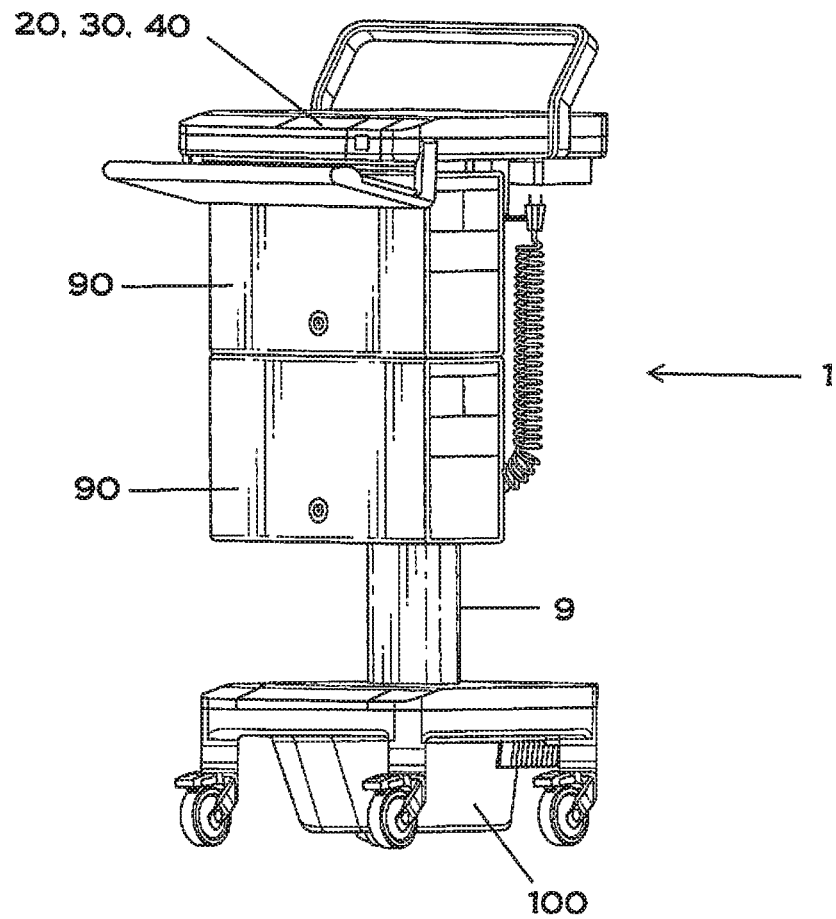
FIG. 11 is another embodiment of the station.

One particular embodiment of the invention is shown in FIG. 11, sometimes referred to as the T7 MedLink Lite or MedLink Lite embodiment ("Lite"). This embodiment uses a T7 cart, but does not necessarily include a separate monitor, keyboard, or laptop. Instead, a tablet, such as the computer tablet built into the T7 work surface may function as the system processor, and memory display and input device (a touch screen). Additional devices may be coupled to the tablet, such as a mouse or scanner. In the Lite version, the cassette's drawers are configured with RFID tags, but proximity sensors are not necessarily needed, unless the Lite embodiment is to be configured for automatic door closure (the sensors may be included, but auto closing functioning may be disabled by the System Administrator). The Lite system can be designed for a single user, so access in this instance is generally by a PIN number or other access code means known to those of ordinary skill in the art. Once the user is logged into the system, the user can open any drawer, or all drawers, by using the touch screen on the tablet to select the drawer(s) to open. In general, the Lite version may only use limited patient identifiers, and is usually not used in a client/server mode. The Lite version is also generally not configured to interface with the hospital's information system network, and thus moving a drawer from one cart to another requires reentry of drawer identifiers in the new cart.

Another particular embodiment is referred to as the T7 MedLink Pro version, such as shown in FIG. 1. In this embodiment, a separate monitor is used as the primary display device, and input devices can include a keyboard, mouse and bar or hash code scanner. The system processor includes a laptop located on the cart, but the cart's computer system may also be configured with wireless interaction with the hospital's network system and a system server. Consequently, certain of the system's software functionality can be running on the hospital server or system server (such as the report generation capability). The preferred T7 cart includes a tablet that controls cart height adjustment, but operation of the cassette functionality in the MedLink Pro version, and interaction with the cassette equipment (proximity sensors, latches, RFID) will normally occur from the cart processor, not the T7 tablet. The Pro version is designed to accommodate multiple UserID/passwords and includes the ability to generate detailed reports on the use of the system, such as UserID usage, patient usage, drawer history, etc. In the MedLink Pro system, all drawers may not be accessible to all users, as some drawers may be assigned to specific UserIDs or user groups. The drawers preferably auto close, and can be opened by selecting a drawer associated patient identifier through interaction with the software, or preferably, by scanning a patient's wristband, where the patient wristband code is associated with a particular drawer or drawers in the configuration map. Multiple identifiers or information items can be associated with each assigned drawer.

Other embodiments of the medical cart may have at least two protection layers for drawers that might contain Schedule II controlled substances. The two or more layer protection may include two layers of security, including one or more locking mechanisms, one or more digital authorization requirements (dual factor authorization), and may require one or more people involved in the authorization process. The authorization process can include a combination of personnel, logical processes, authorizations, physical devices or electronic locking protection Alternatively, a special narcotics cassette drawer or cassette housing could be used to accommodate narcotics.

For instance, if a drawer is to contain heavily regulated narcotics, that drawer could have an additional patient identifier indicating that "narcotics" are contained in the drawer. This identifier could be manually input by the user during operation, or the identifier could be embedded into the RFID tag such that unique RFID tags are used for narcotics drawers. For example, a "narcotics" drawer may be identified as such by the drawer identifier and recognizable as such by reading the identifier (a narcotics drawer may have an identifier that starts with a designated alphanumeric character), or by receiving the drawer status as a "narcotics" drawer from the server computer. This "narcotics" identifier would indicate to the cart that dual layer protection or dual layer authorization is required to open this particular drawer, requiring a second authorization tool be deployed. For instance, a second password or PIN may be required to access the drawer; the system could require the user to verify the user's identify by requiring the user to meet a second identification or credential test, such as fingertip scan, retinal scan, voice identifier or other biometric scan, or to require the user to have a physical authorization identifier or readable token present (such as a RFID tag with a readable userID, a nurse id bracelet with bar code or a hash id that can be scanned by the system; a fob, a badge reader, or other device, such as a digital certificate stored on a smart phone, or a readable card or USB token). The token must be present (e.g. detectable) by the system before access is granted. These tokens or biometric tokens may be held by the same person, or by different persons such that two or more users need to be present to access the narcotics drawer. Alternatively, the system may employ two factor authentication, where the system sends an electronic authorization code to the user's electronic account (such as that user's smart device or hospital email account), and that user has to receive this dynamically assigned authorization code and then enter this authorization code into the cart to provide access.

Dual layer physical electronic/mechanical protection may also be used. For instance, a "narcotics" drawer may have a second physical layer of protection, such as a separate lock (electronic or physical lock, such as a keyed lock) requiring the user to have the key to the second lock Alternatively, the cassettes could have one or more additional separately actuatable latches that are used for narcotics drawers, requiring a two-step unlatching sequence before access is provided. This second latch layer can be combined with separate authorization, e.g. the additional one or more latches is only actuatable by a second properly credentialed user. For a narcotics drawer, the second one or more latches would not open the drawer, but would simply unlock to allow the second one or more mechanical latches to open the drawer. For example, the second latch or latches would unlock first, thereby allowing the first latch or latches described above to unlock and partially open the narcotics drawer. In a dual latching layer system, a separate cassette may be used with all drawers labeled as narcotics drawers, with the cassette backplane and cassette firmware modified to accommodate separate latches. In one embodiment, a similar spring-loaded latch that is used for the ejectable handle for the cassette could be used for the second latching mechanism. The cassette identifier could be labeled as a "narcotics" cassette to allow a cart to recognize this cassette and all drawers as "narcotics", and to required dual authorization as specified in the system. The separate cassette could situated beneath the non-narcotics housing(s) and could be in communication with the computer system in the same manner as the non-narcotics housing(s). The foregoing description and accompanying drawings illustrate the principles, exemplary embodiments, and modes of operation of the invention. However, the invention should not be construed as being limited to the particular embodiments discussed above. Many modifications of the embodiments described herein will come to mind to one skilled in the art having the benefit of the teaching presented in the foregoing descriptions and the associated drawings. For instance, the RFID tags may be replaced with a bar code or hash code, and the RFID reader replaced with a scanner; the proximity sensor may be a capacitance sensor, photo sensor, optical sensor, ultrasonic sensor, or other type of proximity sensor. Instead of addressable electronic communications on a common bus or common communications path, each peripheral sensor or device could have a dedicated communications path, eliminating the need for an addressing scheme and a common bus. but increasing the wiring harness size. As used herein, "electronic communication" encompasses both common bus communication and dedicated individual communications path, or a combination thereof. The station is generally described as a movable cart, however the station may be a fixed station, such as a docking station used in a fixed location described above. Further, in the system as described, the cassette components respond after being polled by the processor. Alternative communications schemes are included in the scope of the invention, such as using an interrupt requests by the peripheral devices to establish communications. Accordingly, it should be appreciated that variations to those embodiments can be made by those skilled in the art without departing from the scope of the invention.

The invention claimed is:

1. A medical station comprising:
   (a) a movable cart;
   (b) a computer system comprising an input device, a display device, and a processor, the computer system positioned on the cart and including computer memory in communication with the processor;
   (c) a housing mounted on the cart;
   (d) at least one portable cassette system removably coupled to the housing, wherein the processor is in electronic communication with the input device, the display device, and the cassette system; and
   (e) wherein the cassette system comprises:
      (i) a cassette frame defining an interior divided into compartments;
      (ii) drawers, each of the drawers occupying, and being slidably positioned in, at least one of the compartments;
      (iii) each of the compartments having an actuator associated therewith in communication with the processor and associated with an actuator latch that is movable in response to operation of the associated actuator;
      (iv) each of the drawers having at least one drawer latch, and each of the drawers capable of moving from a locked and closed position to an unlocked position in response to movement from the associated actuator latch;
      (v) whereby the computer system is configured to automatically transition a specific one of the drawers from the unlocked position to the locked position where the specific one of the drawers remains in the unlocked position for at least a selected period of time.

2. The medical station of claim 1, wherein the computer system is configured to move the specific one of the drawers into the unlocked position by movement of the actuator associated with the specific one of the drawers in response to receipt of an open drawer command for the specific one of the drawers received from the input device.

3. The medical station of claim 1, further comprising electronically readable identifier tags, each associated with one of the drawers and comprising a unique drawer identifier; and
   electronic readers, each associated with one of the drawers and configured to read the identifier tags, wherein the computer system is configured to identify a position of each of the drawers in the cassette frame based on positions of the electronic readers relative to the unique identifiers for the drawers.

4. The medical station of claim 3, whereby in response to a drawer open command, the actuator associated with a specific one of the drawers actuates to move the actuator latch of the specific one of the drawers from the locked and closed position to an unlocked and almost closed position.

5. The medical station of claim 1, further comprising a series of proximity sensors each in electrical communication with the processor, each of the drawers being associated with one of the series of proximity sensors.

6. The medical station of claim 5, wherein the computer system is configured to detect whether one of the drawers is in a closed position or an almost closed position based on output of the proximity sensors.

7. The medical station of claim 3, wherein each of the identifier tags comprise a radio frequency identifier (RFID) tag.

8. The medical station of claim 7, wherein each of the RFID tags also indicate a number of the compartments occupied by an associated one of the drawers.

9. The medical station of claim 7, wherein the computer system is configured to classify a respective one of the drawers as in an open position when the proximity sensor associated with the respective one of the drawers is not detected.

10. The medical station of claim 7, wherein the electronic readers are capable of reading the RFID tag of a first one of the drawers one which is in a closed position, but are not capable of reading the RFID tag of an adjacent one of the drawers when the adjacent one of the drawers is in the closed position.

11. The medical station of claim 10, wherein the electronic readers are configured to read only the RFID tag of the first one of the drawers by way of a low power signal which is incapable of energizing the RFID tag of the adjacent one of the drawers.

12. The medical station of claim 1, wherein the computer system is configured to prevent a second one of the drawers from movement into an opened position when a first one of the drawers is in the opened position, unless the computer system receives at least one of an override command, an administrator access command, or a pharmacy access command.

13. The medical station of claim 1, wherein the cassette system further comprises:
   (a) a spring-loaded graspable handle slidably mounted on the cassette frame for movement between a closed position when the handle is not accessible or graspable by a user and released position; and
   (b) a handle actuator mounted to the housing for moving the handle between the closed position and the released position.

14. The medical station of claim 1, further comprising a configuration map located in the computer memory, the configuration map comprising, for each respective one of the drawers, a unique drawer identifier and an indicator of a location of the respective one of the drawers in an interior of the cassette frame.

15. The medical station of claim 1, wherein the cassette system includes a drawer manual override configured to allow a hardware key to mechanically unlatch all of the actuator latches so that the drawers are capable of opening.

16. The medical station of claim 15, wherein the housing includes a cassette manual override allowing the cassette system to be mechanically unlocked and removed from the housing.

17. The medical station of claim 16, wherein the cassette manual override includes a lockable cassette handle activated by a manual hardware key.

* * * * *